US007351526B2

(12) United States Patent
Soto et al.

(10) Patent No.: US 7,351,526 B2

(45) Date of Patent: Apr. 1, 2008

(54) EARLY DIAGNOSIS OF CONFORMATIONAL DISEASES

(75) Inventors: Claudio Soto, Laconnex (CH); Gabriella Saborio, Ferney-Voltaire (FR)

(73) Assignee: Laboratories Serono SA, Coinsins, Vaud (CH)

( * ) Notice: Subject to any disclaimer, the term of this patent is extended or adjusted under 35 U.S.C. 154(b) by 421 days.

(21) Appl. No.: 10/332,370

(22) PCT Filed: Jun. 13, 2001

(86) PCT No.: PCT/GB01/02584

§ 371 (c)(1), (2), (4) Date: Nov. 16, 2004

(87) PCT Pub. No.: WO02/04954

PCT Pub. Date: Jan. 17, 2002

(65) Prior Publication Data

US 2005/0064505 A1 Mar. 24, 2005

(30) Foreign Application Priority Data

Jul. 7, 2000 (EP) .................................. 00114650
Dec. 20, 2000 (EP) .................................. 00127892
Feb. 7, 2001 (EP) .................................. 01102732

(51) Int. Cl.
*A61K 38/00* (2006.01)
*C07K 16/00* (2006.01)

(52) U.S. Cl. .......................... 435/5; 530/350; 530/402; 436/536

(58) Field of Classification Search ..................... None
See application file for complete search history.

(56) References Cited

U.S. PATENT DOCUMENTS

2006/0263767 A1* 11/2006 Castrillon et al. ............. 435/5

FOREIGN PATENT DOCUMENTS

EP 0391714 A2 10/1990
WO WO 97/16728 5/1997
WO WO 98/16834 4/1998
WO WO 01/00235 A1 1/2001
WO WO 01/46714 A1 6/2001

OTHER PUBLICATIONS

Castilla et al (2006) Methods in Enzymology, vol. 412: 3-21.*

Aguzzi, ,A. (1997). Neuro-immune connection in the spread of pnions in the body? *Lancet* 349, 742-744.

Baldwin et al., (1995). Prion protein isoforms, a convergence of biological and structural investigations. *J. Biol. Chem*. 2 70, 19197-19200.

Baslet et al., (1986) Scrapie and cellular PrP isoforms are encoded by the same chromosomal gene, *Cell* 46:417-428 (1986).

Brown et al., (2001). Blood infectivity and the prospects for a diagnostic screening test in Creutzfeldt-jakob disease. *J. Lab. Clin. Invest*. 137, 5-13.

Bruce et al., (1997). Transmissions to mice indicate that new variant CJD is caused by the BSE agent *Nature* 389, 498-501.

Budka et al., (1995). Neuropathological diagnostic criteria for CreutzfeldtJakob disease (CJD) and other human spongiform. encephalopathies (Prion diseases). *Brain Pathol*. 5, 459-466.

Carrell et al., (1997). Conformational diseases. *Lancet*, 350, 134-138.

Caughey et al., (1997). Scrapie infectivity correlates with converting activity, protease resistance, and aggregation of scrapie-associated prion protein in guanidine denaturation studies. *J. Virol*. 71, 4107-4110.

Cohen et al., (1994). Structural clues to prion replication. *Science* 264, 530-531.

Cohen et al., (1998). Pathologic conformations of prion proteins. *Ann. Rev. Blochem*. 67,793-819.

Cousens et al., (1997). Predicting the CJD epidemic in humans. *Nature* 385, 197-19 8.

Gabriel et al., (1992) Molecular cloning of a candidate chicken prion protein, *Proc. Nad. Acad Sci. USA* 89:9097-9101.

Galvez et al., (1984). Computed tomogmphy findings in 15 cases of Creutzfeldt-Jakob disease with histological verification. *J. Neurol. Neurosurg. Psychiatry* 47, 1244-1246.

Goldmann et al., (1990) Two alleles of a neural protein gene linked to scrapie in sheep, *Proc. Natl. Acad. Sci. USA* 87:2476-2480.

Goldmann et al., (1991) Different forms of the bovine PrP gene have five or six coies of a short, G-C-rich element within the protein-coding exon *J. Gen. Virol*. 72:201-204.

Harmey et al. (1995). The cellular isoform of the prion protein, PrPc, is associated with caveolae in mouse neuroblastoma (N2a) cells. *Biochem. BIophys. Res. Comm*. 210,753-759.

Harris et al., (1991) A prion-like protein from chicken brain copurifies with an acetylcholine receptor-inducing activity, *Proc. Natl. Acad. Sci. USA* 88:7664-7668.

Hill et al., (1997). Diagnosis of new variant Creutzfeldt-jakob disease by tonsil biopsy. *Lancet* 349, 99-100.

Hsich et al., (1996). The 14-3-3 brain protein in cerebrospinal fluid as a marker for transmissible spongiform encephalopathies. *N. Eng. J. Med*. 335, 924.

Jarrett et al., (1993). Seeding "One-dimensional crystallization" of amyloid: a pathogenic mechanism in Alzheimer's disease and scrapie? *Cell* 73, 1055-1058.

Jimi et al., (1992). High levels of nervous system specific protein in the cerebrospinal fluid in patients with early stage Creutzfeldt-jakob disease. *Clin. Chim. Acta* 211, 37.

(Continued)

*Primary Examiner*—Bruce R. Campell
*Assistant Examiner*—Michelle Horning
(74) *Attorney, Agent, or Firm*—Browdy and Neimark, PLLC

(57) ABSTRACT

A method for the diagnosis or detection of conformational diseases by assaying for a marker (the pathogenic conformer) of such diseases in a sample is described, which method comprises a cyclic amplification system to increase the levels of the pathogenic conformer which causes such diseases. In particular, such transmissible conformational diseases may be prion encephalopathies. Assays, diagnostic kits and apparatus based on such methods are also disclosed.

12 Claims, 13 Drawing Sheets

OTHER PUBLICATIONS

Kawashima et al., (1997). Diagnosis of new variant Creutzfeldt-Jakob disease by tonsil biopsy. *Lancet* 350, 68-69.
Kascsak et al., (1987). Mouse polyclonal and monoclonal antibody to scarpie-associated fibril proteins. *J. Virol.*, 61, 3688-3693.
Kocisko et al., (1994). Cell-free formation of protease-resistant prion protein. *Nature* 370, 471-474.
Kocisko et al., (1995). Species specificity in the cell-free conversion of prion protein to protease-resistant forms: a model for the scrapie species barrier. *Proc. Natl. Acad. Sci. USA* 92, 3923-3927.
Kretzschmar et al., (1986), Molecular cloning of a human prion protein cDNA, *DNA* 5:315-324.
Kretzschmar et al., (1992) Molecular cloning of a mink prion protein gene *J. Gen. Virol.* 73:2757-2761.
Locht et al., (1986) Molecular cloning and complete sequence of prion protein cDNA from mouse brain infected with the scrapie agent, *Proc. Nad. Acad. Sci. USA* 83.6372-6376.
Onofrjj et al., (1993). Early MRI findings in Creutzfeld-jakob disease. *J. Neurol.* 240, 423-426.
Pan et al., (1993). Conversion of alpha-helices into -sheets features in the formation of scrapie prion poteins. *Proc. Natl. Acad. Sci.* (*USA*) 90, 10962-10966.
Prusiner,S.B. (1991). Molecular biology of prion diseases. *Science* 252, 1515-1522.
Roos et al., (1973). The clinical characteristics of transmissible Creutzfeldt-jakob disease. *Brain* 96, 1-20.
Saborio et al., (1999). Cell-lysate conversion of prion protein into its protease-resistant isoform. Suggests the participation of a cellular chaperone. *Biochem. Biopbys. Res. Commun.* 258, 470-475.
Safar et al., (1998). Eight prion strais have Prp(Sc) molecules with different conformations. *Nat. Med.* 4, 1157-1165.
Sargiacomo et al., (1993), Signal transducing molecules and glycos)i-phosphatic44inositol-linked proteins form a caveolin-rich insoluble complex in MDCK cells., *J Cell Biol.* Aug;122(4):789-807.
Stahl et al., (1993). Structural studies of the scrapie prion protein using mass spectrometry and amino acid sequencing. *Biochem.* 32, 1991-2002.
Steinhoff et al., (1996). Accuracy and reliability of periodic sharp wave complexes in Creutzfeldt-jakob disease. *Arch. Neurol.* 53, 162.
Telling et al., (1995). Prion propagation in mice expressing human and chimeric PrP transgenes implicates the interaction of cellular PrP with another protein. *Cell* 83, 7990.
Vey et A. (1996), Subcellular colocalization of the cellular and scrapie prion proteins in caveolae-like membranous domains, *Pro. Natl. Acad. Sci. USA*, 93, 14945-14949.
Weber et al., (1997). Diagnosis of Creutzfeld-jakob disease and related human spongiform. encephalopathies. *Biomed. Pharmacother.* 51, 381-387.
Westaway et al., (1994) Homozygosity for prion protein alleles encoding glutamine-171 renders sheep susceptible to natural scrapie *Genes Dev.* 8:959-969.
WHO/EMC/ZDI/98.9, Global Surveillance, Diagnosis and Therapy of Human Transmissible Spongiform Encephalopathies: Report of a WHO Consultation, Geneva, Switzerland Feb. 9-11, 1998, WHO.
Caughey et al., (1995) Aggresgates of scrapie-associated prion protein induce the cell-free conversion of protease-sensitive prion protein to the protease-resistant state, *Chemistry & Biology*, 2:807-817.
Saborio et al., (1999) Cell-lysate conversion of prion protein into its protease-resistant isoform suggests the participation of a cellular chaperone, *Biochemical and Biophysical Research Communications*, 258,470-475.
Bessen et al., (1995) Non-genetic propagation of strain-specific properties of scrapie prion protein, *Nature*, 375:698-700.
Kocisko et al., (1996) Partial unfolding and refolding of scrapie-associated prion protein: Evidence for a critical 16-kDa C-terminal domain, *Biochemistry*, 35, 13434-13442.
Cohen et al., (1998) Pathologic conformations of prion proteins, *Annu. Rev. Biochem.*, 67:793-819.
Aguzzi et al., (1997) Prion research the next frontiers, *Nature*, 389:795-798.
Iniguez et al., (2000) Strain-specific propagation of $PrP^{Sc}$ properties into baculovirus-expressed hamster $PrP^{c}$, *Journal of General Virology*, 1,2565-2571.
Saborio et al., (2001) Sensitive detection of pathological prion protein by cyclic amplification of protein misfolding, *Nature*, 411:810-813.
Bellotti et al., (2001) Protein aggregation, *Medline/Nlm.* 39, 1065-1075.
Gregersen et al., (2000) Defective folding and rapid degradation of mutant proteins is a common disease mechanism n genetic disorders, *Medline/Nlm*, 23:441-447.
Serpell et al., (2000) Direct visualization of the β-sheet structure of synthetic Alzheimer's amyloid, *J. Mol. Biol.*, 299,225-231.
Soto, (1999) Alzheimer's and prion disease as disorders of protein conformation:implications for the design of novel therapeutic approaches, *J. Mol. Med.*, 77:412-418.
Dumery et al., (2001) β-Amyloid protein aggregation: its implication in the physiopathology of Alzheimer's disease, *Pathol. Biol.*, 49,72-85.

* cited by examiner

Schematic representation of PrPC → PrPSc conversion

Amplification of $PrP^{Sc}$ by sonication cycles

Sensitivity of the cyclic amplification system

Relationship between the PrPres signal and the number of amplification cycles

Scrapie brain homogenate diluted $10^{-2}$ in healthy hamster brain homogenate

Amplification cycles 0 5 10 20 40

Amplification of $PrP^{Sc}$ in blood

Amplification - + - + - + - + - +

Dilution 40 80 160 640 1280

The elements needed for amplification are in lipid rafts

Cyclic amplification of human PrPSc

Blood detection of PrPSc after preparation of blood cells ghosts

Blood detection of PrPSc after sarkosyl extraction

Blood detection of PrPSc after lipid raft purification

Blood detection of PrPSc after preparation of buffy coats

EARLY DIAGNOSIS OF CONFORMATIONAL DISEASES

FIELD OF THE INVENTION

The present invention relates to a method for the diagnosis or detection of conformational diseases by assaying for a marker (i.e. the pathogenic conformer) of such diseases within a sample, which method comprises a cyclic amplification system to increase the levels of the pathogenic conformer. In particular, such conformational diseases may be prion encephalopathies.

BACKGROUND OF THE INVENTION

Conformational diseases are a group of disorders apparently unrelated to each other, but sharing a striking similarity in clinical presentations that reflect their shared molecular mechanisms of initiation and self-association, with consequent tissue deposition and damage.

The structural interest is due to the fact that these varied diseases each arise from an aberrant conformational transition in an underling protein, characteristically leading to protein aggregation and tissue deposition. Medically, the presentation of these conformational diseases reflects this molecular mechanism, with typically a slow and insidious onset when the transition is occurring in a normal protein, but a more sudden onset when it occurs in an unstable variant of the protein. Two examples of special significance of such conformational diseases are the Transmissible Spongiform Encephalopathies and Alzheimer dementia, a disease that threatens to overwhelm health care systems in the developed world (for a review see Carrell et al., 1997).

Transmissible spongiform encephalopathies (TSE) also known as prion diseases are a group of neurodegenerative diseases that affect humans and animals. Creutzfeldt-Jakob disease (CJD), kuru, Gerstmann-Straussler-Scheiker disease (GSS) and fatal familial insomnia (FFI) in humans as well as scrapie and bovine spongiform encephalopathy (BSE) in animals are some of the TSE diseases (Prusiner, 1991).

Although these diseases are relatively rare in humans, the risk for the transmissibility of BSE to humans through the chain food has taken the attention of the public health authorities and the scientific community (Cousens et al., 1997, Bruce et al., 1997).

These diseases are characterized by an extremely long incubation period, followed by a brief and invariably fatal clinical disease (Roos et al., 1973). To date no therapy is available.

The key characteristic of the disease is the formation of an abnormally shaped protein named $PrP^{Sc}$, which is a post-translationally modified version of a normal protein, termed $PrP^{C}$ (Cohen and Prusiner, 1998). Chemical differences have not been detected to distinguish between PrP isoforms (Stahl et al., 1993) and the conversion seems to involve a conformational change whereby the α-helical content of the normal protein diminishes and the amount of β-sheet increases (Pan et al., 1993). The structural changes are followed by alterations in the biochemical properties: $PrP^{C}$ is soluble in non-denaturing detergents, $PrP^{Sc}$ is insoluble; $PrP^{C}$ is readily digested by proteases, while $PrP^{Sc}$ is partially resistant, resulting in the formation of a N-terminally truncated fragment known as "PrPres" (Baldwin et al., 1995; Cohen and Prusiner, 1998), "PrP 27-30" (27-30 kDa) or "PK-resistant" (proteinase K resistant) form.

At present there is not an accurate diagnosis for TSE (WHO Report, 1998, Budka et al., 1995, Weber et al., 1997).

Attempts to develop a diagnostic test for prion diseases are hampered by the apparent lack of an immune response to $PrP^{Sc}$. The clinical diagnosis of CJD is based upon the combination of subacute progressive dementia (less than 2 years), myoclonus, and multifocal neurological dysfunction, associated with a characteristic periodic electroencephalogram (EEG) (WHO Report, 1998, Weber et al., 1997). However, variant CJD (vCJD), most of the iatrogenic forms of CJD and up to 40% of the sporadic cases do not have the EEG abnormalities (Steinhoff et al., 1996). On average the accuracy of clinical diagnosis is around 60% for CJD and highly variable for other prion-related diseases. The clinical diagnosis is more accurate only at the late-stage of the disease when clear symptoms have developed (Weber et al., 1997).

Genetic analysis is useful for the diagnosis of inherited prion diseases, but these represent only 15% of the cases. Neuroimaging is useful only to exclude other conditions of rapidly progressive dementia due to structural lesions of the brain (Weber et al., 1997). The findings obtained by imaging of the brain by computed tomography (CT) and magnetic resonance imaging (MRI) depend mainly on the stage of the disease. CT is much less sensitive and in early phase no atrophy is detected in 80% of the cases (Galvez and Cartier, 1983). MRI hyperintense signals have been detected in the basal ganglia besides atrophy (Onofrji et al., 1993). Like the changes observed by CT, these alterations are by no means specific.

Recent data have identified several neuronal, astrocytic and glial proteins that are elevated in CJD (Jimi et al., 1992). The protein S-100, neuron specific isoenzyme and ubiquitin are significantly increased in the cerebrospinal fluid (CSF) in the early phase of disease with decreasing concentrations over the course of the illness (Jimi et al., 1992). A marker of neuronal death, the 14-3-3 protein, has been proposed as a specific and sensitive test for sporadic CJD (Hsich et al., 1996). However, it is not useful for the diagnosis of vCJD, and much less specific in the genetic forms. As the 14-3-3 protein may be present in the CSF of patients with other conditions, the test is not recommended by WHO as a general screening for CJD and is reserved to confirm the clinical diagnosis (WHO Report, 1998).

By combining clinical data with the biochemical markers a higher success in the diagnosis is achieved. However, according to the operational diagnosis currently in use in the European Surveillance of CJD, definitive diagnosis is established only by neuropathological examination and detection of $PrP^{Sc}$ either by immunohistochemistry, histoblot or western blot (Weber et al., 1997, Budka et al., 1995).

Formation of $PrP^{Sc}$ is not only the most likely cause of the disease, but it is also the best known marker. Detection of $PrP^{Sc}$ in tissues and cells correlates widely with the disease and with the presence of TSE infectivity, and treatments that inactivate or eliminate TSE infectivity also eliminate $PrP^{Sc}$ (Prusiner, 1991). The identification of $PrP^{Sc}$ in human or animal tissues is considered key for TSE diagnosis (WHO Report, 1998). One important limitation to this approach is the sensitivity, since the amounts of $PrP^{Sc}$ are high (enough for detection with conventional methods) only in the CNS at the late stages of the disease. However, it has been demonstrated that at earlier stages of the disease there is a generalized distribution of $PrP^{Sc}$ (in low amounts), especially in the lymphoreticular system (Aguzzi, 1997). Indeed, the presence of $PrP^{Sc}$ has been reported in palatine tonsillar tissue and appendix obtained from patients with vCJD (Hill et al., 1997). Although it is not known how early in the disease course tonsillar or appendix biopsy could be used in vCJD diagnosis, it has been shown that in sheep genetically susceptible to scrapie, $PrP^{Sc}$ could be detected in tonsillar tissue presymptomatically and early in the incubation period. However, $PrP^{Sc}$ has not been detected in these tissues so far in any cases of sporadic CJD or GSS (Kawashima et al., 1997).

The normal protein is expressed in white blood cells and platelets and therefore it is possible that some blood cells may contain $PrP^{Sc}$ in affected individuals (Aguzzi, 1997). This raises the possibility of a blood test for CJD, but this would require an assay with a much greater degree of sensitivity than those currently available.

Prion replication is hypothesized to occur when $PrP^{Sc}$ in the infecting inoculum interacts specifically with host $PrP^{C}$, catalyzing its conversion to the pathogenic form of the protein (Cohen et al., 1994). This process takes from many months to years to reach a concentration of $PrP^{Sc}$ enough to trigger the clinical symptoms.

The infective unit of $PrP^{Sc}$ seems to be a β-sheet rich oligomeric structure, which converts the normal protein by integrating it into the growing aggregate (FIG. 1). The conversion has been mimicked in vitro by mixing purified $PrP^{C}$ with a 50-fold molar excess of previously denatured $PrP^{Sc}$ (Kocisko et al., 1994).

The in vitro conversion systems described so far have low efficiency, since they require an excess of $PrP^{Sc}$ and therefore are not useful for diagnostic purposes because they cannot monitor undetectable amounts of the marker. The reason for the low efficiency is that the number of $PrP^{Sc}$ oligomers (converting units) remains fixed throughout the course of the assay. The converting units grow sequentially by the ends and as a result they become larger, but do not increase in number (FIG. 1).

DETAILED DESCRIPTION OF THE INVENTION

We have now found a method for the diagnosis or detection of a conformational disease, wherein the disease is characterized by a conformational transition of an underlying protein between a non-pathogenic and a pathogenic conformer, by assaying a marker of said disease within a sample, which method comprises:

(i) contacting said sample with an amount of the non-pathogenic conformer;

(ii) disaggregating any aggregates eventually formed during step (i); and (iii) determining the presence and/or amount of said pathogenic conformer within the sample.

Generally, the pathogenic conformer will be the marker for the presence of the said disease.

Preferably, step (i) comprises step (ia) incubating said sample/non-pathogenic conformer.

According to a preferred embodiment of the invention, steps (ia) and (ii) form a cycle which is repeated at least twice before carrying out step (iii). More preferably, the cycles are repeated from 5 to 40 times, and most preferably 5-20 times.

The conformational diseases to be detected or diagnosed are those that are characterised by a conformational transition of an underlying protein. This "underlying protein" is a protein which is capable of adopting a non-pathogenic conformation and a pathogenic conformation. One example of such a protein is the prion protein, PrP. A further example of such a protein is the protein involved in Alzheimer's disease, i.e. the β-amyloid protein.

The conformational diseases to be diagnosed or detected are preferably transmissible conformational diseases, such as TSE (as defined in the Background section).

In the case of diagnosis of TSE and according to a preferred embodiment of the invention, the marker of the disease as well as the pathogenic conformer is $PrP^{Sc}$, whereas the non-pathogenic conformer of the protein of interest is $PrP^{C}$.

The amount of the non-pathogenic conformer that is used in step (i) (and optionally in step (ib)) will generally be a known amount, although this need not be the case if one merely wishes to establish the presence or absence of the pathogenic conformer.

Preferably, the amount of non-pathogenic conformer that is used in step (i) (and optionally in step (ib)) will be an excess amount. Generally, the initial ratio of non-pathogenic conformer to pathogenic conformer (if present in the sample) will be greater than 100:1, preferably greater than 1000:1 and most preferably greater than 1000000:1.

In a further preferred embodiment of the invention, the non-pathogenic conformer in step (i) is present in a brain homogenate of a healthy subject and/or may be added to it, before carrying out step (i); in this case, therefore, the brain homogenate containing a (preferably known) excess of the non-pathogenic conformer is added during step (i). Preferably, the brain homogenate of the healthy subject comes from the same species from which the sample to be analyzed comes (e.g. human brain homogenate for human sample to be analyzed, rat brain homogenate from rat sample to be analyzed). More preferably, the non-pathogenic conformer is present in a specific fraction of the brain homogenate, for example in the lipid-rafts from brain homogenate. The preparation of such fractions can be carried out for example as described in Sargiacomo M et al., 1993.

Thus the invention further relates to a method or assay as described herein wherein a tissue or tissue fraction is added to the non-pathogenic conformer in step (i). Preferably, the tissue is brain tissue, or a homogenate or fraction derived therefrom, from a healthy subject (i.e. one where the pathogenic conformer is not present).

It has been reported (Kocisko et al., 1994) that less glycosylated forms of $PrP^{C}$ are preferentially converted to the $PrP^{Sc}$ form. In particular, $PrP^{C}$ which was treated with phosphatidylinositol specific phospholipase C was routinely more efficiently converted to the pathogenic form than the complete, more heavily glycosylated $PrP^{C}$. A further embodiment of the invention therefore relates to a method or assay as herein described wherein the non-pathogenic conformer is $PrP^{C}$ which has a reduced level of glycosylation (in particular N-linked glycosylation) in comparison with the wild-type $PrP^{C}$. Preferably, the $PrP^{C}$ has been treated to remove some, all or a significant amount of the glycosylation prior to its use as the non-pathogenic conformer in the methods and assays described herein; and more preferably, the non-pathogenic conformer is $PrP^{C}$ which is essentially unglycosylated.

In the case of diagnosis of TSE, if aggregates of the pathogenic form are present within the sample, during step (i) they will induce the $PrP^{C} \rightarrow PrP^{Sc}$ transition and during step (ii) such aggregates will be broken down into smaller still infective units, each of which is still capable of inducing the conversion of other $PrP^{C}$. This kind of method is herein called "cyclic amplification" and is represented in FIG. 2. This system results in an exponential increase in the amount of $PrP^{Sc}$ eventually present in the sample that can easily be detected. According to a further preferred embodiment of the invention, it is therefore possible to calculate the amount of $PrP^{Sc}$ initially present in the sample starting from the known amount of $PrP^C$, determining the amount of $PrP^{Sc}$ present within the sample at the end of the assay and considering the number of cycles performed.

If, on the contrary, no $PrP^{Sc}$ (either as such or in the form of aggregates) is present in the sample, no $PrP^C$ molecule will be converted into $PrP^{Sc}$ and at the end of the assay the marker will be completely absent (no pathogenic conformer detected in the sample).

It has been shown that the infective unit of $PrP^{Sc}$ is a β-sheet rich oligomer, which can convert the normal protein by integrating it into the growing aggregate, where it acquires the properties associated with the abnormal form (protease resistance and insolubility) (Jarrett and Lansbury, Jr., 1993, Caughey et al., 1997). After incubation of the two forms of PrP, the oligomeric species increases its size by recruiting and transforming $PrP^C$ molecules. This process has low efficiency, since it depends on a fixed number of oligomers growing by the ends. The number of converting units is not increased in the course of the reaction when they only become larger. It is assumed that this process is what happens in the animal or human body after infection; a process known to take months or even several years. In this invention we describe a procedure to break down the oligomers to a smaller ones, each of which is then capable of converting $PrP^C$.

Therefore, the system has direct applications to the diagnosis of conformational diseases, and in particular transmissible conformational diseases, such as TSE by amplifying otherwise undetectable amounts of $PrP^{Sc}$ in different tissues or biological fluids. The system may allow the early identification of people at risk of developing TSE and could also be very useful to follow biochemically the efficacy of TSE therapeutic compounds during clinical trials.

According to a preferred embodiment of the invention the sample to be analysed is subjected to a "pre-treatment" step, which has the purpose of "selectively concentrating" in the sample the pathogenic conformer that is to be detected. In the case of TSE both $PrP^C$ and $PrP^{Sc}$ have been reported to be located in a special region of the plasma membrane which is resistant to mild detergent treatment (such as ice-cold Triton X-100) due to the relatively high content of cholesterol and glycosphingolipids (M. Vey et al., 1996). These membrane domains are named lipid-rafts or detergent-resistant membranes (DRM) or caveolae-like domains (CLDs) and are rich in signaling proteins, receptors and GPI-anchored proteins. We have confirmed that 100% of $PrP^C$ in brain is attached to this fraction, which contains <2% of the total proteins (see Example 6 and FIG. 7). Thus, the simple step of lipid-raft isolation from the sample allows a dramatic enrichment in $PrP^C$. Similar results were obtained by the Applicant in the isolation of lipid-rafts from scrapie brain homogenate, in which $PrP^{Sc}$ was recovered in the rafts.

Thus one embodiment of the invention includes a step wherein the sample to be analysed is subjected to a pre-treatment step for selectively concentrating the pathogenic conformer in the sample. Preferably, the pathogenic conformer is $PrP^{Sc}$ and the pretreatment is the extraction from the sample of a fraction which is insoluble in mild detergents.

Steps (i) and (ia) are preferably performed under physiological conditions (pH, temperature and ionic strength) and, more preferably, protease inhibitors and detergents are also added to the solution. The conditions will be chosen so as to allow any pathogenic conformer, if present in the sample, to convert the non-pathogenic conformer into pathogenic conformer thus forming an aggregate or oligomer of pathogenic conformers. Appropriate physiological conditions will readily be apparent to those skilled in the art.

The length of the incubation will be for a time which will allow some, all or a significant portion of the non-pathogenic conformer to be converted to pathogenic conformer, assuming that the sample contains some pathogenic conformer. The time will readily be determinable by those skilled in the art. Preferably, each incubation will be between 1 minute to 4 hours, most preferably 30 minutes to 1 hour, and particularly preferably approximately 60 minutes.

Incubation step (ia) may also comprise the further step (ib) which comprises the addition of a further amount of non-pathogenic conformer.

Various methods can be used for disaggregating the aggregates during step (ii) of the method of the present invention. They include: treatment with solvents (such as sodium dodecyl sulfate, dimethylsulfoxide, acetonitrile, guanidine, urea, trifluoroethanol, diluted trifluroacetic acid, diluted formic acid, etc.), modification of the chemical-physical characteristics of the solution such as pH, temperature, ionic strength, dielectric constant, and physical methods, such as sonication, laser irradiation, freezing/thawing, French press, autoclave incubation, high pressure, stirring, mild homogenization, other kinds of irradiation, etc. Sonication is the preferred method according to the invention Disaggregation may be carried out for a time which disaggregates some, all or a significant portion of the aggregates which have formed during step (ii). It is not necessary for all of the aggregates to be disaggregated in any one disaggregation step. In this way, the number of converting units is increased in each disaggregation step.

The disaggregation time will readily be determinable by those skilled in the art and it may depend on the method of disaggregation used. Preferably, disaggregation is carried out for 1 second to 60 minutes, most preferably 5 seconds to 30 minutes and particularly preferably, 5 seconds to 10 minutes. If disaggregation is carried out by sonication, sonication is preferably for 5 seconds to 5 minutes, and most preferably for 5 to 30 seconds.

Sonication has been used in the past as part of several methods to purify PrP with the goal of increasing solubility of large aggregates, but it has never been described to amplify in vitro conversion of PrP.

The use of a traditional single-probe sonicator imposes a problem for handling many samples simultaneously, such as a diagnostic test will require. There are on the market some 96-well format microplate sonicators, which provide sonication to all the wells at the same time and can be programmed for automatic operation. These sonicators can be easily adapted to be used in the diagnostic method of the present invention.

Thus one embodiment of the invention relates to the use, in step (ii), of a multi-well sonicator.

The detection of the newly converted pathogenic conformer, e.g. $PrP^{Sc}$, (iii) after the cyclic amplification procedure described in steps (i) to (ii) could be carried out according to any of the known methods. Specific detection of $PrP^{Sc}$ is usually (but not always, see below) done by a first step of separation of the two PrP isoforms (normal protein and pathogenic protein). Separation is done on the basis of the peculiar biochemical properties of $PrP^{Sc}$ that distinguish it from most of the normal proteins of the body, namely: $PrP^{Sc}$ is partially resistant to protease treatment and is insoluble even in the presence of non-denaturant detergents. Therefore the first step after the amplification procedure is usually the removal or separation of $PrP^C$ in the sample, either by treatment with proteases or by centrifugation to separate the soluble ($PrP^C$) from the insoluble ($PrP^{Sc}$) protein. Thereafter, detection of $PrP^{Sc}$ can be done by any of the following methods, inter alia:

A) Immunobloting after SDS-PAGE. This is done through a routine procedure well known for those with skill in the art and using some of the many commercially available anti-PrP antibodies.

B) Elisa assay. Solid phase detection can be done by either a simple assay in which the sample is loaded on the plate and the amount of $PrP^{Sc}$ detected afterwards by using anti-PrP antibodies or more preferably by using sandwich Elisa in which the plate is first coated with an anti-PrP antibody that captures specifically PrP from the sample, which is finally detected by using a second anti-PrP antibody. Both forms of Elisa can also be used with labelled (radioactivity, fluorescence, biotin, etc) anti-PrP antibodies to further increase the sensitivity of the detection.

C) Radioactivity assays. Normal $PrP^C$ used as a substrate for the amplification procedure can be radioactively labelled (3H, 14C, 35S, 125I, etc) before starting the procedure and after the removal of the non-converted $PrP^C$, radioactivity of newly converted $PrP^{Sc}$ could be quantitated. This procedure is more quantitative and does not rely on the use antibodies.

D) Fluorescence assays. Normal $PrP^C$ used as a substrate for the amplification procedure can be labelled with fluorescent probes before starting the procedure and after the removal of non-converted $PrP^C$, fluorescence of the newly converted $PrP^{Sc}$ could be quantitated. It is possible that the fluorescence assay might not require the removal of non-converted $PrP^C$, because the fluorescence properties of $PrP^C$ and $PrP^{Sc}$ might be different due to the distinct conformation of the two isoforms.

E) Aggregation assays. It is well known that $PrP^{Sc}$ (and not $PrP^C$) is able to aggregate forming amyloid fibrils or rod-type structures. Therefore detection of $PrP^{Sc}$ could be done by using the methods used to quantify the formation of these type of aggregates, including electron microscopy, staining with specific dyes (Congo red, Thioflavin S and T, etc), and turbidimetric assays. Aggregation assays do not require the step of separation of the two isoforms, because is known that normal PrPC does not aggregate.

F) Structural assays. The most important difference between the normal and the pathogenic PrP is their secondary and tertiary structures. Therefore, methods that allow the structural evaluation of proteins can be used, including NMR, Circular dichroism, Fourier-transformed infrared spectroscopy, Raman spectroscopy, intrinsic fluorescence, UV absorption, etc.

The most widely used PrP monoclonal antibody is "3F4" (Kascsak et al., 1987), which is a monoclonal antibody derived from a mouse immunized with hamster 263K PrPres (the protease-resistant conformer). This antibody is also able to recognize the non-pathogenic conformer from hamsters and humans, but not from bovine, mouse, rat, sheep or rabbit brains; it is also able to bind the human pathogenic conformer, but only after denaturation of the protein.

Such antibodies may be labeled to allow easy detection of the marker. For example time-resolved fluorescence measurements with europium-labeled 3F4 antibody has been used by some scientists (Safar et al., 1998).

The above-described methods of detection may be used for the detection of other pathogenic conformers, for example the pathogenic form of β-amyloid protein, mutatis mutandis.

In an alternative embodiment the non-pathogenic conformer added in excess may be labeled and detectable so that the amount of the non-aggregated conformer at the end of the assay will allow a determination of the amount of pathogenic conformer initially present in the sample.

According to a further alternative embodiment, the pathogenic conformer (the marker) could be directly detected with an antibody directed against it.

In broader terms a label or labeling moiety may be added to the pathogenic conformer, to the non-pathogenic conformer or to an antibody against one of the conformers depending on the kind of assay that is performed.

Another object of the invention is an assay for a marker of a conformational disease which is characterized by a conformational transition of an underlying protein between a non-pathogenic and a pathogenic conformer, within a sample, which assay comprises the following steps: (i) contacting said sample with an amount of the non-pathogenic conformer, (ii) disaggregating any aggregates eventually formed during step (i) and (iii) determining the presence and/or amount of said pathogenic conformer within the sample. In general, the pathogenic conformer will be the marker for the presence of said disease.

Preferably, step (i) comprises step (ia) incubating said sample/non-pathogenic conformer.

According to a preferred embodiment of the invention, steps (ia) and (ii) form a cycle which is repeated at least twice before carrying out step (iii). More preferably, the cycles are repeated from 5 to 40 times, and most preferably 5 to 20 times.

A further object of the present invention is a diagnostic kit for use in the assay specified, which comprises an amount of the non-pathogenic conformer, and optionally additionally a micro-titre plate and a multi-well sonicator.

Using the method of the invention, it is possible to detect 1 to 10 fg of pathogenic conformer initially present in a sample, which is equivalent to 3 to $30\times10^{-20}$ moles.

The sample will generally be a biological sample or tissue, and any such biological sample or tissue can be assayed with the method of the present invention. In the case of a tissue, the assay and method of the present invention may be carried out on homogenates or direct on ex vivo samples. The methods and assays will generally be carried out on ex vivo or in vitro samples. Preferably, the sample is a biological fluid, such as blood, lymph, urine or milk; brain tissue, spinal cord, tonsillar tissue or appendix tissue; a sample derived from blood such as blood cell ghosts or buffy coat preparations; or a plasma membrane preparation such as lipid-rafts, detergent resistant membranes or caveolae-like domains. The sample might alternatively be a composition comprising a compound (particularly a protein) derived from a human or animal source, such as growth hormone, or a tissue extract, such as pituitary extract. Such a sample composition might be contaminated with a pathogenic conformer.

The sample might also comprise a food product or drink, or a portion of a food product or drink (either destined for human consumption or animal consumption) in order to establish the presence or absence of pathogenic conformer in that product or drink.

Preferably, the non-pathogenic conformer added in step (i) will be from the same species as the sample. It may, for example, be derived from a healthy (i.e. non-pathogenic) form (e.g. tissue) of the biological sample to be tested. Alternatively, the non-pathogenic conformer may be produced synthetically or recombinantly, using means known in the art. It will be understood, however, that the non-pathogenic conformer need not be in pure or even substantially pure form. In most cases, the non-pathogenic conformer will be in the form of a tissue homogenate or a fraction thereof which contains the relevant non-pathogenic conformer. Preferred examples include brain homogenates and fractions derived therefrom, e.g. lipid rafts.

Preferably, the sample and/or the non-pathogenic conformer will be of human origin or from a domestic animal, e.g. a cow, sheep, goat or cat.

Another object of the present invention is to provide a method for identifying a compound which modulates the conformational transition of an underlying protein between a non-pathogenic and a pathogenic conformer, comprising:

(i) contacting an amount of the non-pathogenic conformer with an amount of the pathogenic conformer in the presence and in the absence of said compound, (ii) disaggregating any aggregates eventually formed during step (i), (iii) determining the amount of the pathogenic conformer in the presence and in the absence of said compound.

If desired, step (i) may comprise step (ia) incubating said sample/non-pathogenic conformer, and a cycle carried out between steps (ia) and (ii) as described above for the methods and assays of the invention, mutatis mutandis.

If the amount of pathogenic conformer measured in the presence of the compound is higher than that measured in the absence, it means that the compound is a factor which "catalyzes" the conformational transition; if such amount is lower, it means that the compound is a factor which inhibits such transition.

According to the above method, "identifying" should also be interpreted to mean "screening" of a series of compounds.

A "label" or "labelling moiety" may be any compound employed as a means for detecting a protein. The label or labelling moiety may be attached to the protein via ionic or covalent interactions, hydrogen bonding, electrostatic interactions or intercalation. Examples of labels and labelling moieties include, but are not limited to fluorescent dye conjugates, biotin, digoxigenin, radionucleotides, chemiluminescent substances, enzymes and receptors, such that detection of the labelled protein is by fluorescence, conjugation to streptaviden and/or avidin, quantitation of radioactivity or chemiluminescence, catalytic and/or ligand-receptor interactions. Preferably it is a fluorescent or a phosphorescent label.

The term "conformational diseases" refers to that group of disorders arising from a propagation of an aberrant conformational transition of an underlying protein, leading to protein aggregation and tissue deposition. Such diseases can also be transmitted by an induced conformational change, propagated from a pathogenic conformer to its normal or non-pathogenic conformer and in this case they are called herein "transmissible conformational diseases". Examples of such kinds of diseases are the prion encephalopathies, including the bovine spongiform encephalopathy (BSE) and its human equivalent Creutzfeld-Jakob (CJD) disease, in which the underlying protein is the PrP.

The term "sporadic CJD" abbreviated as "sCJD" refers to the most common manifestation of Creutzfeldt-Jakob Disease (CJD). This disease occurs spontaneously in individuals with a mean age of approximately 60 at a rate of 1 per million per year individuals across the earth.

The term "Iaterogenic CJD" abbreviated as "iCJD" refers to disease resulting from accidental infection of people with human prions. The most noted example of such is the accidental infection of children with human prions from contaminated preparations of human growth hormone.

The term "Familial CJD" refers to a form of CJD, which occurs rarely in families and is inevitably caused by mutations of the human prion protein gene. The disease results from an autosomal dominant disorder. Family members who inherit the mutations succumb to CJD.

The term "Gerstmann-Strassler-Scheinker Disease" abbreviated as "GSS" refers to a form of inherited human prion disease. The disease occurs from an autosomal dominant disorder. Family members who inherit the mutant gene succumb to GSS.

The term "prion" shall mean a transmissible particle known to cause a group of such transmissible conformational diseases (spongiform encephalopathies) in humans and animals. The term "prion" is a contraction of the words "protein" and "infection" and the particles are comprised largely if not exclusively of $PrP^{Sc}$ molecules.

Prions are distinct from bacteria, viruses and viroids. Known prions include those which infect animals to cause scrapie, a transmissible, degenerative disease of the nervous system of sheep and goats as well as bovine spongiform encephalopathies (BSE) or mad cow disease and feline spongiform encephalopathies of cats. Four prion diseases known to affect humans are (1) kuru, (2) Creutzfeldt-Jakob Disease (CJD), (3) Gerstmann-Strassler-Scheinker Disease (GSS), and (4) fatal familial insomnia (FFI). As used herein prion includes all forms of prions causing all or any of these diseases or others in any animals used and in particular in humans and in domesticated farm animals.

The terms "PrP gene" and "prion protein gene" are used interchangeably herein to describe genetic material which expresses the prion proteins and polymorphisms and mutations such as those listed herein under the subheading "Pathogenic Mutations and Polymorphisms." The PrP gene can be from any animal including the "host" and "test" animals described herein and any and all polymorphisms and mutations thereof, it being recognized that the terms include other such PrP genes that are yet to be discovered.

The term "PrP gene" refers generally to any gene of any species which encodes any form of a PrP amino acid sequences including any prion protein. Some commonly known PrP sequences are described in Gabriel et al., 1992, which is incorporated herein by reference to disclose and describe such sequences.

Abbreviations used herein include:

CNS for central nervous system;

BSE for bovine spongiform encephalopathy;

CJD for Creutzfeldt-Jakob Disease;

FFI for fatal familial insomnia;

GSS for Gerstmann-Strassler-Scheinker Disease;

PrP for prion protein;

$PrP^C$ for the normal, non-pathogenic conformer of PrP;

$PrP^{Sc}$ for the pathogenic or "scrapie" isoform of PrP (which is also the marker for prion diseases).

Pathogenic Mutations and Polymorphisms

There are a number of known pathogenic mutations in the human PrP gene. Further, there are known polymorphisms in the human, sheep and bovine PrP genes.

The following is a non-limiting list of such mutations and polymorphisms:

MUTATION TABLE

| Pathogenic human mutations | Human polymorphisms | Sheep polymorphisms | Bovine polymorphisms |
|---|---|---|---|
| 2 octarepeat insert | Codon 129 Met/Val | Codon 171 Arg/Glu | 5 or 6 octarepeats |
| 4 octarepeat insert | Codon 219 Glu/Lys | Codon 136 Ala/Val | |

-continued

MUTATION TABLE

| Pathogenic human mutations | Human polymorphisms | Sheep polymorphisms | Bovine polymorphisms |
|---|---|---|---|
| 5 octarepeat insert | | | |
| 6 octarepeat insert | | | |
| 7 octarepeat insert | | | |
| 8 octarepeat insert | | | |
| 9 octarepeat insert | | | |
| Codon 102 Pro-Len | | | |
| Codon 105 Pro-Leu | | | |
| Codon 117 Ala-Val | | | |
| Codon 145 Stop | | | |
| Codon 178 Asp-Asn | | | |
| Codon 180 Val-Ile | | | |
| Codon 198 Phe-Ser | | | |
| Codon 200 Glu-Lys | | | |
| Codon 210 Val-Ile | | | |
| Codon 217 Asn-Arg | | | |
| Codon 232 Met-Ala | | | |

The normal amino acid sequence, which occurs in the vast majority of individuals, is referred to as the wild-type PrP sequence. This wild-type sequence is subject to certain characteristic polymorphic variations. In the case of human PrP, two polymorphic amino acids occur at residues 129 (Met/Val) and 219 (Glu/Lys). Sheep PrP has two amino acid polymorphisms at residues 171 and 136, while bovine PrP has either five or six repeats of an eight amino acid motif sequence in the amino terminal region of the mature prion protein. While none of these polymorphisms are of themselves pathogenic, they appear to influence prion diseases. Distinct from these normal variations of the wild-type prion proteins, certain mutations of the human PrP gene which alter either specific amino acid residues of PrP or the number of octarepeats have been identified which segregate with inherited human prion diseases.

In order to provide further meaning to the above chart demonstrating the mutations and polymorphisms, one can refer to the published sequences of PrP genes. For example, a chicken, bovine, sheep, rat and mouse PrP gene are disclosed and published within Gabriel et al., 1992. The sequence for the Syrian hamster is published in Baslet et al 1986. The PrP gene of sheep is published by Goldmann et al., 1990. The PrP gene sequence for bovine is published in Goldmann et al., 1991. The sequence for chicken PrP gene is published in Harris et al., 1991. The PrP gene sequence for mink is published in Kretzschmar et al., 1992. The human PrP gene sequence is published in Kretzschmar et al., 1986. The PrP gene sequence for mouse is published in Locht et al., 1986. The PrP gene sequence for sheep is published in Westaway et al., 1994. These publications are all incorporated herein by reference to disclose and describe the PrP gene and PrP amino acid sequence.

The invention also provides a method for detecting the presence of a pathogenic form of prion protein within a sample (preferably a blood or brain sample) comprising:

(i) contacting the sample with an amount of non-pathogenic prion protein;

(ia) incubating the sample/non-pathogenic prion protein;

(ii) disaggregating any aggregates formed during step (ia); repeating steps (ia)-(ii) two or more times; and then (iii) determining the presence and/or amount of pathogenic prion protein within the sample.

A further embodiment of the invention provides a method for diagnosing CJD within a patient, comprising: taking a sample from the patient (preferably a blood or brain sample);

(i) contacting the sample with an amount of $PrP^C$ protein;

(ia) incubating the sample/$PrP^C$ protein;

(ii) disaggregating any aggregates formed during step (ia); repeating steps (ia)-(ii) two or more times; and then (iii) determining the presence and/or amount of $PrP^{Sc}$ within the sample.

The invention also provides a method for detecting the presence of a pathogenic form of β-amyloid protein within a sample (preferably a blood or brain sample), comprising:

(i) contacting the sample with an amount of non-pathogenic β-amyloid protein;

(ia) incubating the sample/non-pathogenic β-amyloid protein;

(ii) disaggregating any aggregates formed during step (ia); repeating steps (ia)-(ii) two or more times; and then (iii) determining the presence and/or amount of pathogenic β-amyloid protein within the sample.

A further embodiment of the invention provides a method for diagnosing Alzheimer's disease in a patient, comprising: taking a sample (preferably a blood or brain sample) from the patient;

(i) contacting the sample with an amount of non-pathogenic β-amyloid protein;

(ia) incubating the sample/non-pathogenic β-amyloid protein;

(ii) disaggregating any aggregates formed during step (ia); repeating steps (ia)-(ii) two or more times; and then (iii) determining the presence and/or amount of pathogenic β-amyloid protein within the sample.

The invention furthermore provides apparatus for use in the methods described above, particularly apparatus comprising a microtitre plate, multi-well sonicator and an amount of a non-pathogenic conformer.

A further embodiment of the invention provides a method for the diagnostic detection of a conformational disease, characterized by a conformational transition of an underlying protein between a non-pathogenic and a pathogenic conformer, by assaying a marker of said disease within a sample, which method comprises (i) contacting said sample with a known amount of the non-pathogenic conformer, (ii) disaggregating the aggregates eventually formed during step (i) and (iii) determining the presence and/or amount of said pathogenic conformer within the sample. Preferably, steps (i) and (ii) form a cycle which is repeated at least twice before carrying out step (iii), most preferably steps (i) and (ii) form a cycle, which is repeated from 5 to 40 times before carrying out step (iii).

The invention also provides an assay for a marker of a conformational disease, characterized by a conformational transition of an underlying protein between a non-pathogenic and a pathogenic conformer, within a sample, which assay comprises the following steps: (i) contacting said sample with a known amount of the non-pathogenic conformer, (ii) disaggregating the aggregates eventually formed during step (i) and (iii) determining the presence and/or amount of said pathogenic conformer within the sample. Preferably, the steps (i) and (ii) form a cycle which is repeated at least twice before carrying out step (iii).

The invention further provides a method for identifying a compound which modulates the conformational transition of an underlying protein between a non-pathogenic and a pathogenic conformer, comprising:

(i) contacting a known amount of the non-pathogenic conformer with a known amount of the pathogenic conformer in the presence and in the absence of said compound,
(ii) disaggregating the aggregates eventually formed during step (i),
(iii) determining the amount of the pathogenic conformer in the presence and in the absence of said compound.

The present invention has been described with reference to the specific embodiments, but the content of the description comprises all modifications and substitutions, which can be brought by a person skilled in the art without extending beyond the meaning and purpose of the claims.

The invention will now be described by means of the following Examples, which should not be construed as in any way limiting the present invention. The Examples will refer to the Figures specified here below.

EXAMPLES

Example 1

Amplification of PK Resistant PrP by Cyclic in vitro Conversion

Figure 1:
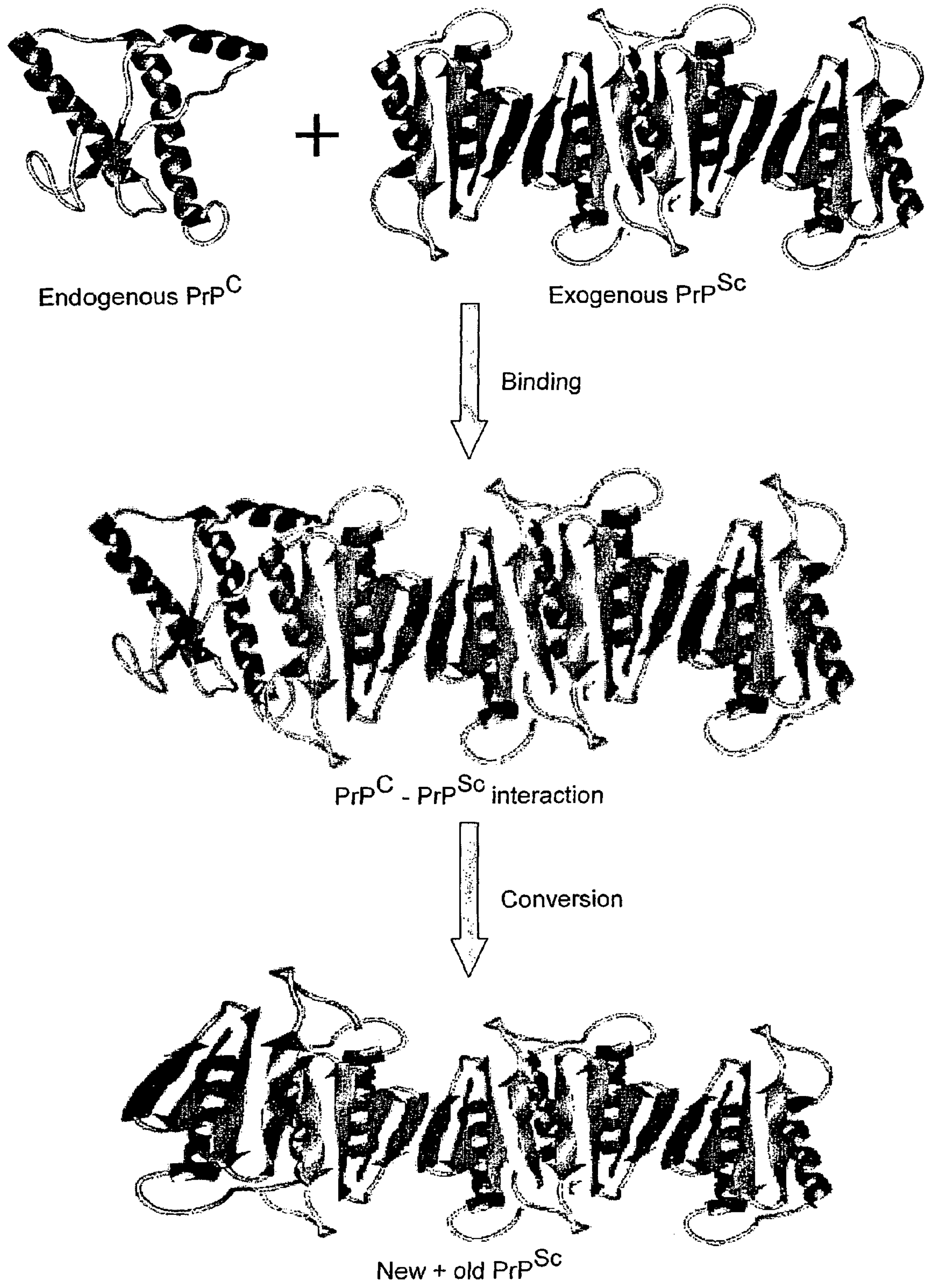
FIG. 1. Schematic representation of the conversion $PrP^{C} \rightarrow PrP^{Sc}$. The infective unit of $PrP^{Sc}$ is a β-sheet rich oligomer, which converts $PrP^{C}$ by integrating it into the growing aggregate, where it acquires the properties associated with $PrP^{Sc}$.
Figure 2:
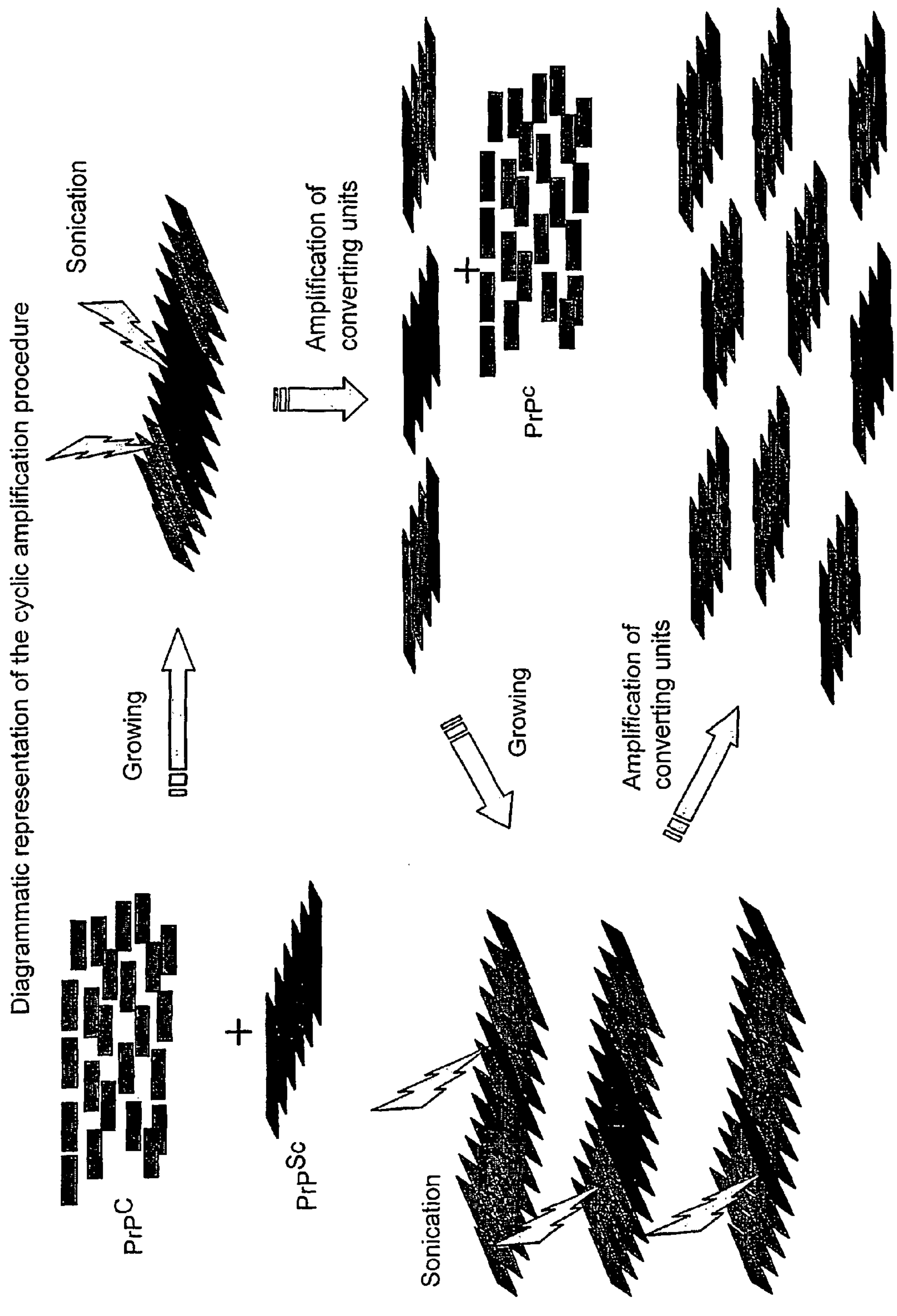
FIG. 2. Diagrammatic representation of the cyclic amplification procedure. The system is based on cycles of incubation of $PrP^{Sc}$ in the presence of excess of $PrP^{C}$ followed by cycles of sonication. During the incubation periods, oligomeric $PrP^{Sc}$ is enlarged by incorporating $PrP^{C}$ into the growing aggregate, while during sonication the aggregates are sonication/incubation are shown.
Figure 3:
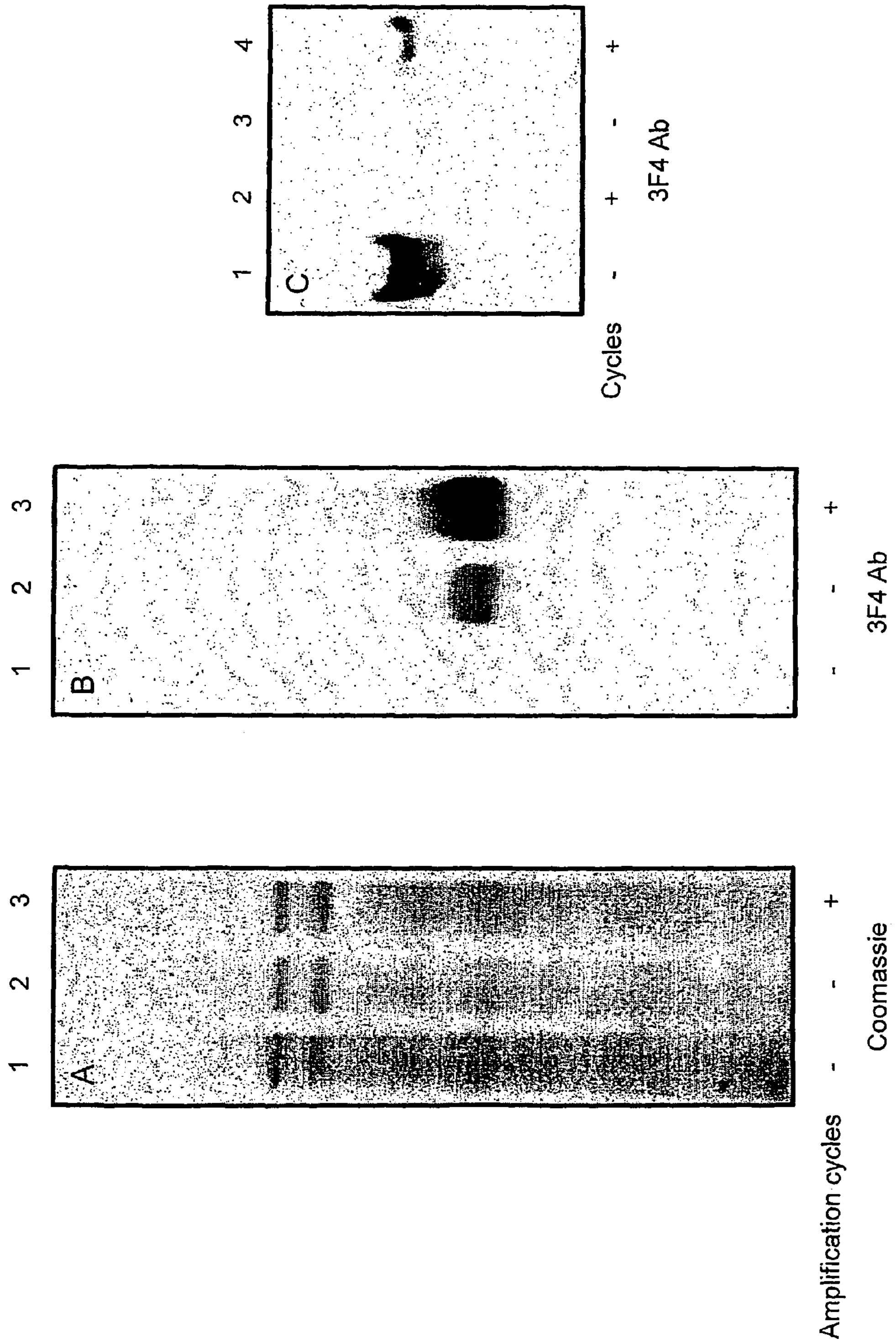
FIG. 3. Amplification of $PrP^{Sc}$ by sonication cycles. A small amount of scrapie brain homogenate containing $PrP^{Sc}$ was incubated with healthy rat brain homogenate (lane 1, control experiment) or with healthy hamster brain homogenate (lane 2 and 3). The latter sample was divided in two groups one of which was subjected to five cycles of incubation/sonication (lane 3). Half of the above samples were loaded directly in a gel and stained for total protein with Coomasie (panel A). The other half were treated with PK and immunoblotted using the anti-PrP antibody 3F4 (panel B). Panel C shows some controls in which healthy brain homogenate was incubated alone (lanes 1 and 2) or in the presence of diluted scrapie brain homogenate (lanes 3 and 4). Half of the samples (lanes 2 and 4) were subjected to 5 cycles of sonication/incubation. Lanes 2, 3 and 4 were treated with proteinase K.

Hamster brain homogenate extracted from scrapie affected animals was diluted until the signal of $PrP^{Sc}$ was barely detected by immunoblot after treatment with proteinase K (PK) FIG. 3B, lane 1). PK treatment is done routinely in the field to distinguish between the normal and abnormal forms of PrP, which differ in their sensitivity to protease degradation ($PrP^{Sc}$ is partially resistant and $PrP^{C}$ is degraded) (Prusiner, 1991). The form of PrP that is resistant to PK treatment will be named from now on PrPres. Incubation of a sample of diluted scrapie brain homogenate with a healthy hamster brain homogenate containing an excess of $PrP^{C}$, resulted in the increase in PrPres signal (FIG. 3B, lane 2).

This suggests that the incubation of the two brain homogenates resulted in the conversion of $PrP^{C}$ to $PrP^{Sc}$. When the samples were incubated under the same conditions but subjected to five cycles of incubation/sonication, the amount of PrPres was dramatically increased (FIG. 3B, lane 3). Densitometric analysis of the immunoblot indicates that the PrPres signal was increased 84-fold by cyclic amplification in comparison with the PrPres signal presented in the diluted scrapie brain homogenate (lane 1).

The conversion is dependent of the presence of $PrP^{Sc}$ since no PrPres was observed when the normal hamster brain homogenate was incubated alone under the same conditions either with or without sonication (FIG. 3C, lane 2). To rule out artifacts of the transfer, the total protein loaded in the gel was maintained constant (FIG. 3A) by adding rat brain homogenate to the diluted scrapie sample, taking advantage of the fact that rat PrP is not detected by the antibody used for the immunoblot.

Example 2

Sensitivity of Detection by Cyclic Amplification

Figure 4:
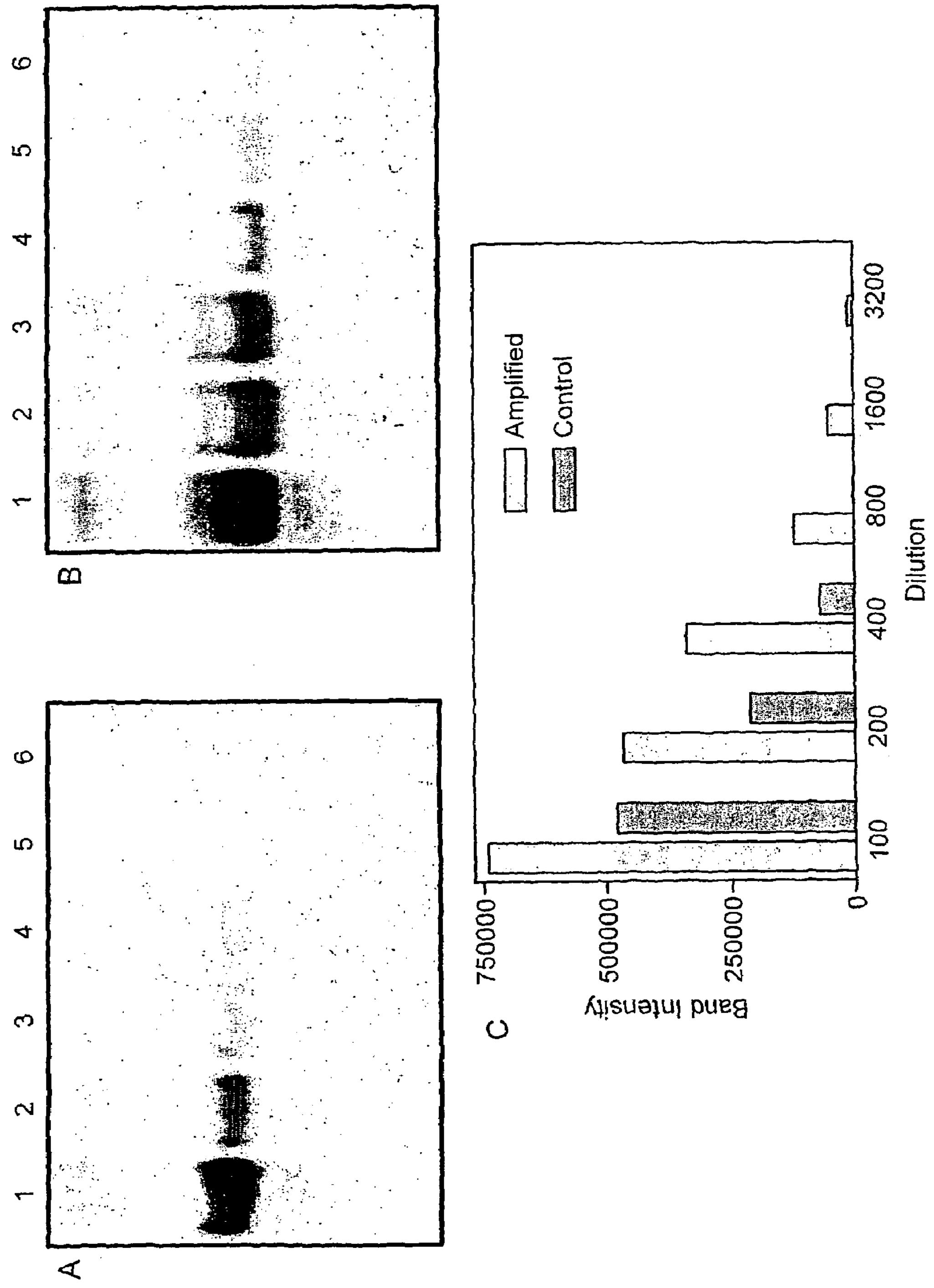
FIG. 4. Sensitivity of the cyclic amplification system. The minimum concentration of $PrP^{Sc}$ that can be used for detection after amplification was studied by serially diluting the scrapie brain homogenate and incubating with healthy hamster brain homogenate with or without sonication cycles. Panel A shows the control experiment in which scrapie hamster brain was diluted serially in rat brain homogenate. Panel B corresponds to the experiment in which the serial dilutions of scrapie hamster brain were incubated with healthy hamster brain and subjected to 5 cycles of incubation/sonication. Densitometric evaluation of the immunoblots in A and B is shown in panel C. The dilutions were done considering as starting material the brain and were the following: 100 (lane 1), 200 (lane 2), 400 (lane 3), 800 (lane 4), 1600 (lane 5) and 3200 (lane 6).

To evaluate the minimum concentration of $PrP^{Sc}$ that can be used for detection after amplification, the scrapie brain homogenate was serially diluted directly in healthy hamster brain homogenate. Without incubation, the signal of PrPres diminishes progressively until it was completely undetectable at 800-fold dilution (FIGS. 4A, C). In contrast when the same dilution was incubated with healthy hamster brain homogenate and subjected to 5 cycles of incubation/sonication, the limit of PrPres detection was decreased dramatically. Indeed, clear signal was easily detected even at a 3200-fold dilution (FIGS. 4B, C).

Example 3

Exponential Increase in PrPres with Number of Cycles

Figure 5:
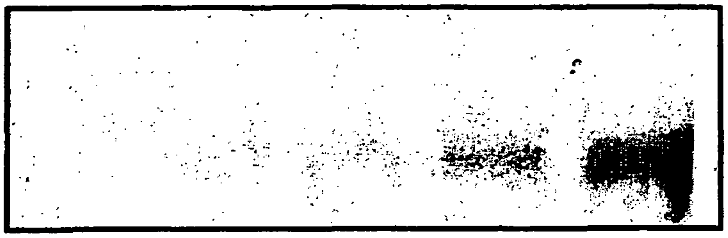
FIG. 5. Relationship between the PrPres signal and the number of amplification cycles. Diluted scrapie brain homogenate was incubated with an excess of healthy hamster brain homogenate. Samples were subjected to 0, 5, 10, 20 or 40 cycles and the PrPres signal evaluated by immunoblot.

To study whether the intensity of the PrPres signal after cyclic amplification depends on the number of cycles of incubation/sonication performed, diluted scrapie brain homogenate was incubated with an excess of healthy hamster brain homogenate. Samples were subjected to 0, 5, 10, 20 or 40 cycles and the PrPres signal evaluated by immunoblot. The levels of PrPres increased exponentially with the number of incubation/sonication cycles (FIG. 5). This result suggests that increasing the number of cycles could further diminish detection limits.

Example 4

Sonication Experiments in Blood Samples by Spiking with $PrP^{Sc}$

Heparinized rat blood was spiked with Scrapie hamster brain homogenate to reach a final dilution of 10:1. This mixture was incubated for 15 min at RT.

10 fold serial dilutions were made of this material using heparinized rat blood. 50 μl of each dilution were centrifuged at 3,000 rpm for 10 min. Plasma was separated from the pellet. 10 μl of plasma were mixed in 50 μl of healthy hamster brain homogenate containing the $PrP^{C}$ substrate for the conversion reaction. Samples were subjected to 11 cycles of incubation-sonication. As a control same samples were mixed in 50 μl of healthy hamster brain homogenate and kept at −20° C. until needed. 15 μl of sonicated and control samples were digested with proteinase K, separated by SDS-PAGE and analyzed by western blotting and $PrP^{Sc}$ was detected as disclosed in the "Methods" section.

Figure 6:
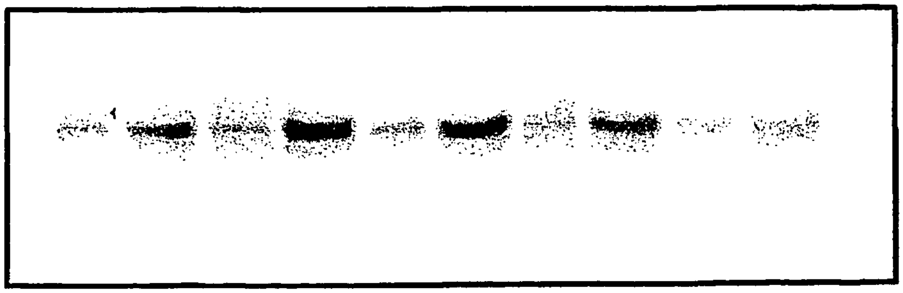
FIG. 6. Amplification of $PrP^{Sc}$ in blood samples. Heparinized rat blood was spiked with Scrapie hamster brain homogenate to reach a final dilution of 10:1. This mixture was incubated for 15 min at RT. 10 fold serial dilutions were made of this material using heparinized rat blood. Samples were subjected to 11 cycles of incubation-sonication and the PrPres signal evaluated by immunoblot.

The results are reported in FIG. 6. These results show a clear increase in the detection of the protein after the amplification procedure, which is especially evident at the lower concentration of $PrP^{Sc}$ (for example at the 1280 dilution). If we compare such results with those obtained on infected brain tissues, we have the confirmation that the amplification process works similarly in blood.

Example 5

High Throughput Cyclic Amplification

The use of a single-probe traditional sonicator imposes a problem for handling many samples simultaneously, as a diagnostic test will require. We have adapted the cyclic amplification system to a 96-well format microplate sonicator (Misonix 431MP- 20 kHz), which provides sonication to all of the wells at the same time and can be programmed for automatic operation. This improvement not only decreases processing time, but also prevents loss of material when compared to using a single probe. Cross contamination is eliminated since there is no direct probe intrusion into the sample. The latter is essential to handle infectious samples and minimize false positive results. Twenty cycles of 1 h incubation followed by sonication pulses of 15 sec or 30 sec gave a significant amplification of PrPres signal, similar to that previously observed using a traditional sonicator.

Example 6

Figure 7:
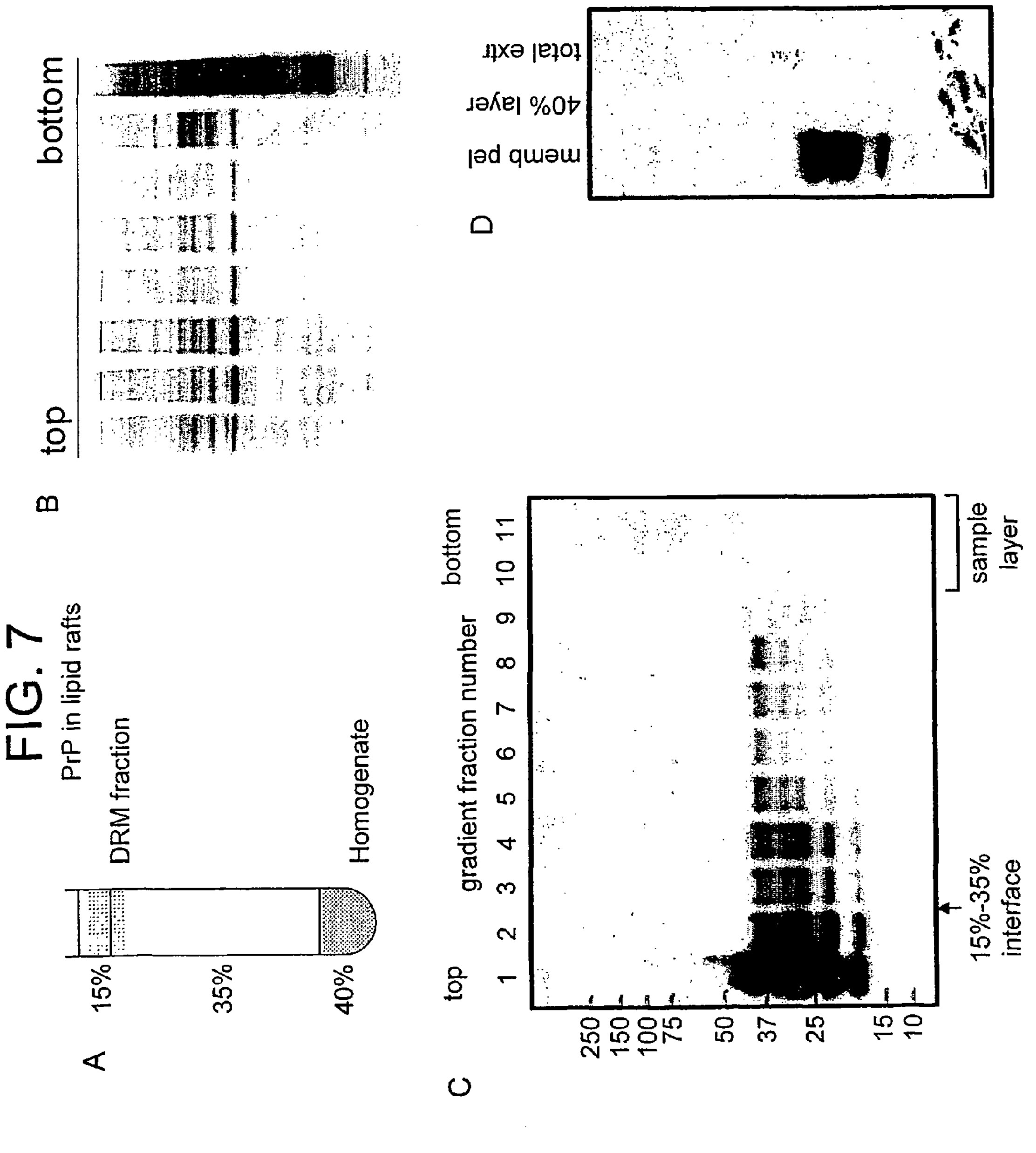
FIG. 7: Prion protein is present in lipid-rafts. Lipid-rafts (also called detergent-resistant membrane fraction or DRM) were isolated using a modification of previouly described protocols. One-hundred mg of brain tissue was homogenized in 1 ml of PBS containing 1% triton X-100 and 1× complete cocktail of protease inhibitors (Boehringer). Tissue was homogenized with 10 passages through 22 G syringe needle and incubated for 30 minutes at 4° C. on a rotary shaker. The sample was diluted 1:2 in sucrose 60% and placed in the bottom of a centrifuge tube. 7 ml of sucrose 35% were place carefully over the sample. 1.5 ml of sucrose 15% was layered in the top of the gradient. The tube was centrifuged at 150,000 g for 18 hrs at 4° C. The lipid rafts float to the 15%-35% sucrose interface (panel A). Different fractions were collected and analyzed by total protein staining with silver nitrate (panel B) and immunoblot to detect PrP (panel C). To remove sucrose from the sample, lipid raft fraction was recovered washed in PBS and centrifuged at 28,000 rpm during 1 hr at 4° C. The pellet was washed and resuspended in PBS containing 0.5% Triton X-100, 0.5% SDS and protease inhibitors. All PrPC was located in this fraction (panel D).

The Factors Necessary for Amplification Are in a Detergent-Resistant Membrane Fraction The subcellular location where the PrP conversion occurs during the disease pathogenesis is not yet ascertained. However, both $PrP^C$ and $PrP^{Sc}$ have been reported to be located in a special region of the plasma membrane which is resistant to mild detergent treatment due to the relatively high content of cholesterol and glycosphingolipids (Vey et al., 1996; Harmey et al., 1995). These membrane domains are named lipid-rafts or detergent-resistant membranes (DRM) and are rich in signaling proteins, receptors and GPI-anchored proteins. We have confirmed that 100% of PrPC in brain is attached to this fraction, which contains <2% of the total proteins (FIG. 7). Thus, the simple step of lipid-raft isolation allows a dramatic enrichment in $PrP^C$. Similar results were obtained in the isolation of lipid-rafts from scrapie brain homogenate, in which $PrP^{Sc}$ was recovered in the rafts.

Figure 8:
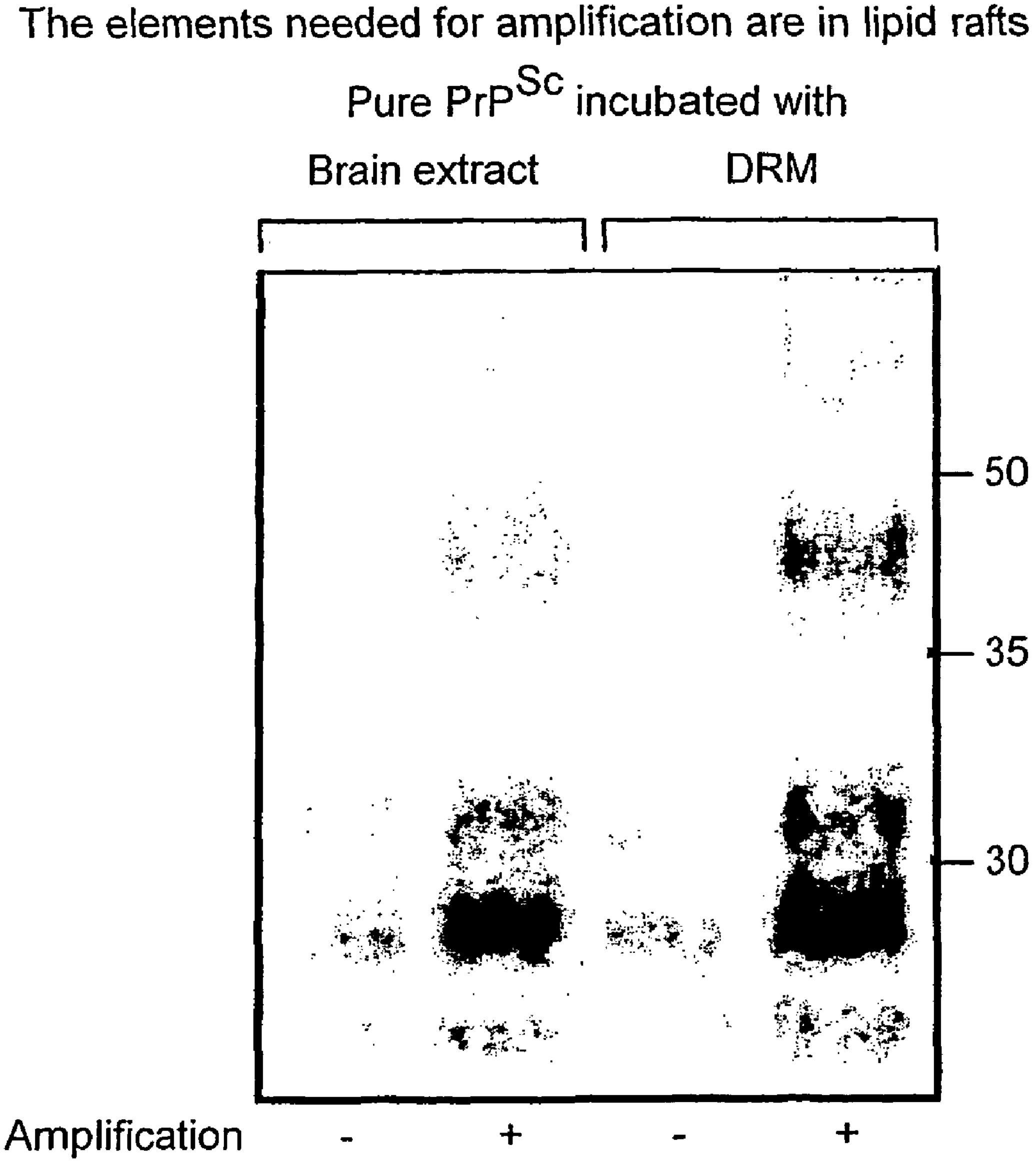
FIG. 8: The factors needed for amplification are present in lipid-rafts. Lipid-rafts were isolated from healthy hamster brain as describe in FIG. 2 and mixed with 700-fold diluted PrPSc highly purified from scrapie hamster brain. Samples were either frozen (line 3) or amplified for 20 h (line 4). Lines 1 and 2 represent the same procedures but using total brain homogenate for amplification.

To evaluate whether the factors needed to amplify PrP are contained in lipid-rafts, we purified them from the brain of healthy animals and added minute quantities of highly pure $PrP^{Sc}$ extracted from the brain of sick animals. Amplification in lipid-rafts was equivalent to that obtained with total brain extract (FIG. 8), since the amount of PrPres produced after amplification was similar in both conditions. This result indicates that all elements required for PrP conversion and amplification (including the so-called "Factor X"; (Telling et al., 1995)) are contained in this specialized membrane domain. Therefore, identification and isolation of the factors needed for PrP conversion should be possible by further separation of proteins from the lipid-rafts and monitoring their activity by cyclic amplification. In addition, lipid-rafts constitute a possible replacement for the use of total brain homogenate in the cyclic amplification procedure as a source of $PrP^C$ substrate and other endogenous factors implicated in the conversion.

Example 7

Pre-Symptomatic Diagnosis in Experimental Animals

Figure 9:
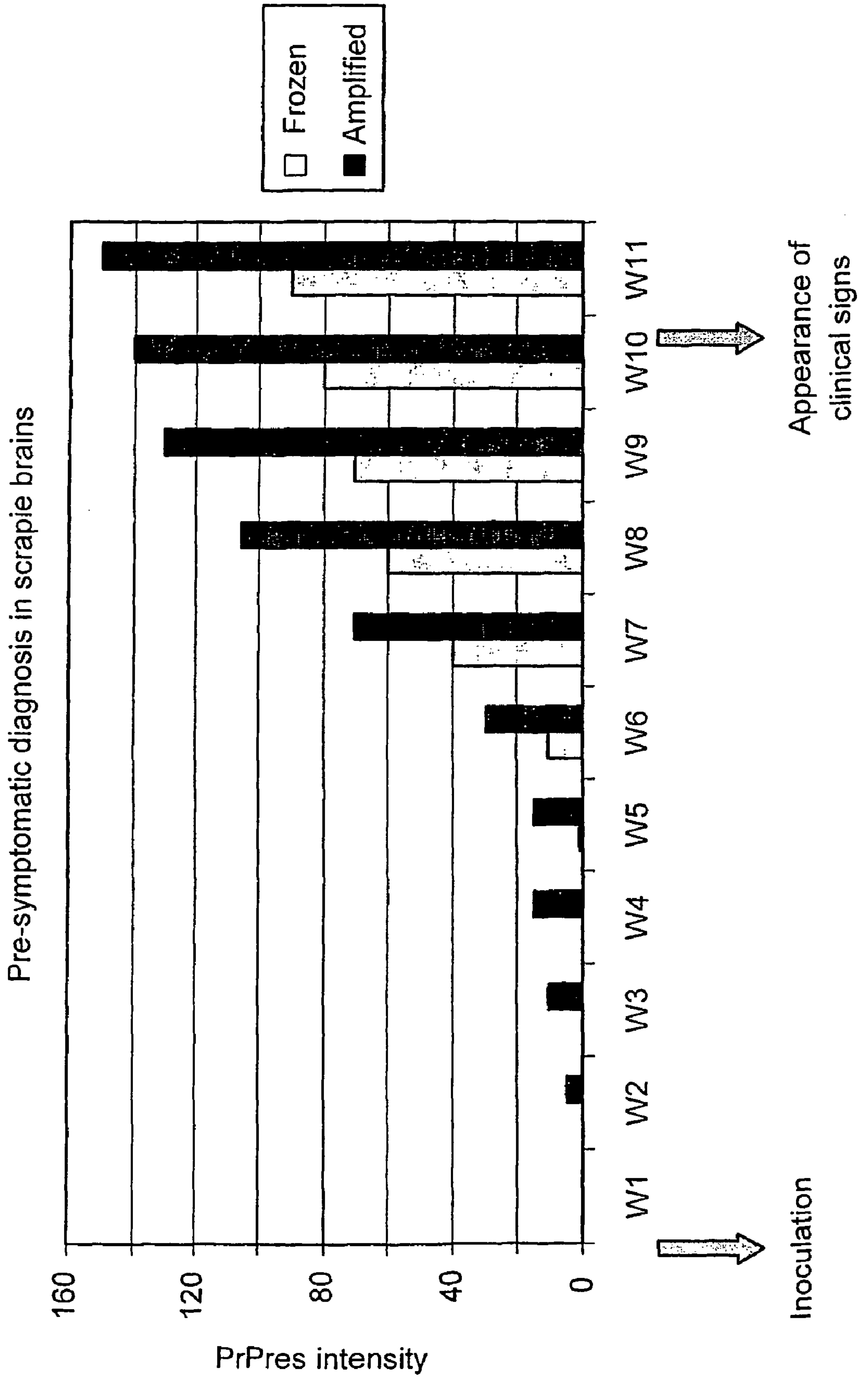
FIG. 9: Presymptomatic detection of PrPSc in hamster brain. Hamsters were inoculated intra-cerebrally (i.c.) with saline (control group) or with 100-fold diluted scrapie brain homogenate. Every week 4 hamsters per group were sacrificed and brains were extracted and homogenized. Half of the samples were frozen immediately (white bars) and the other half subjected to 20 cycles of incubation/sonication (black bars). All samples were treated with PK and immunoblotted. The intensity of the bands was evaluated by densitometry. Each bar represent the average of samples from 4 animals. No detection was observed in any of the control brains either without or with amplification and these results are not shown in the Figure.

To study the pre-symptomatic diagnosis of hamsters experimentally infected with scrapie, we screened 88 brain samples at different stages during the preclinical phase, half of which were non-infected controls. Brain was taken every week (4 per each group) and subjected to 20 cycles of amplification. The results showed that the method is able to detect the abnormal protein in the brain even at the second week after inoculation, far before the animals develop any symptoms (FIG. 9). Without cyclic amplification, $PrP^{Sc}$ was detected in the brain at week six post-infection, only 4 weeks before the appearance of the clinical disease. No amplification was detected in any of the control animals that were not infected with scrapie.

Example 8

Application of Cyclic Amplification to Human Brain Samples

Figure 10:
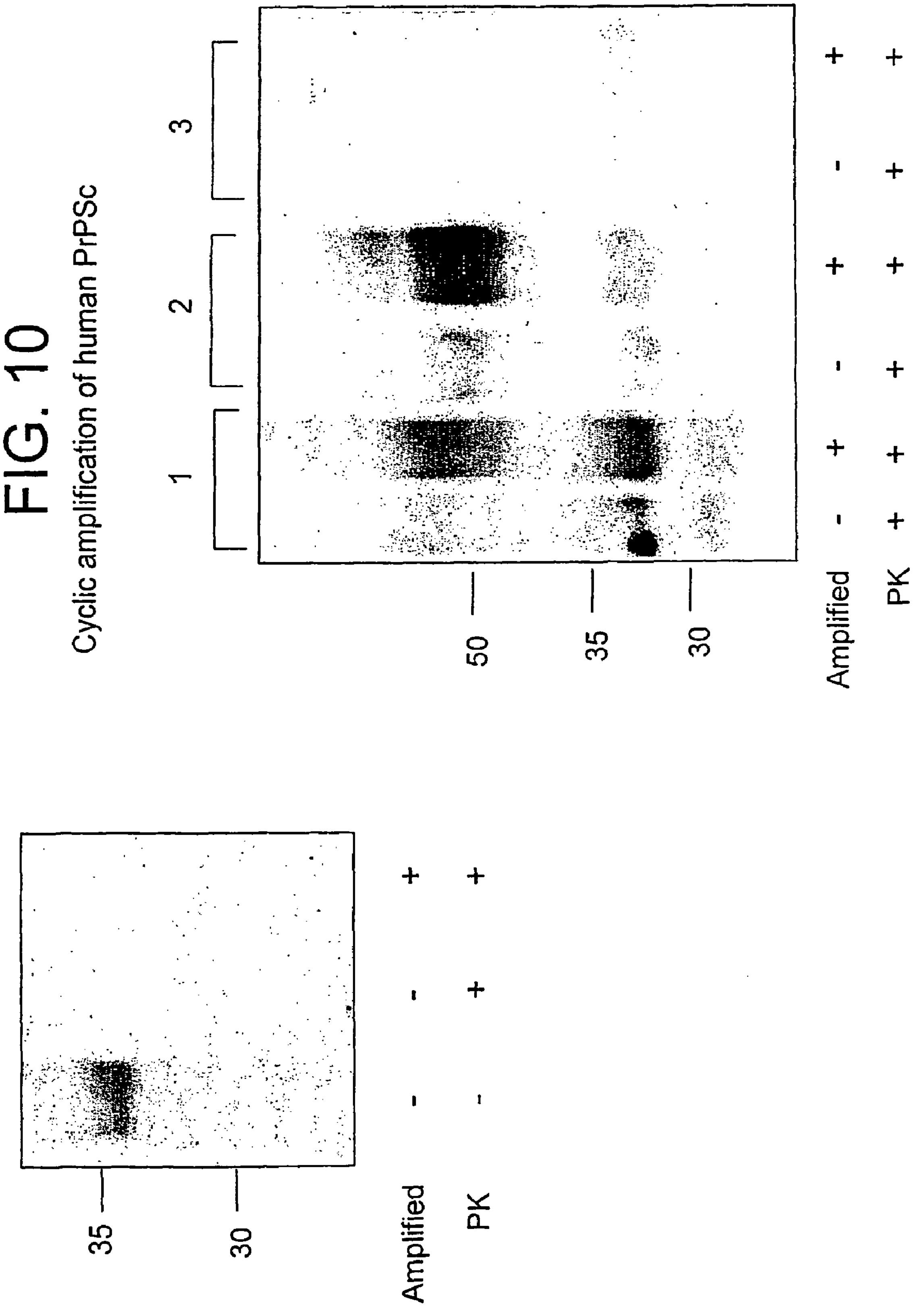
FIG. 10: Amplification of human PrPSc. The studies were done using brain samples of 11 different confirmed cases of sporadic CJD, as well as 5 from familial CJD and 4 age-matched controls, which included patients affected by other neurological disorders. Brain was homogenized and subjected to 20 amplification samples. Representative results of a control (A) and three different sporadic CJD (B) cases (1, 2, 3) are shown in the Figure.

To analyze the application of the cyclic amplification procedure to human samples from brain of people (cadavers) affected by Creutzfeldt-Jakob disease (CJD), we incubated brain homogenates of several CJD patients (or normal controls) with healthy human brain homogenate and carried out the cyclic amplification procedure. The results show that there was significant amplification in samples of sporadic CJD brain analyzed and in none of the 4 control samples (FIG. 10). Interestingly, amplification was obtained only in the samples that had shown to be infectious and thus able to convert non-mutated $PrP^C$, while it did not work when the mutant protein is not capable to convert the wild type protein. These data support the conclusion that the method works in human samples similarly as shown before for animal samples.

Example 9

Diagnosis in Blood by Cyclic Amplification

Infectivity studies suggested that at least in experimental animals $PrP^{Sc}$ is present in blood in late-stage animals (Brown et al., 2001). In order to perform the blood detection of $PrP^{Sc}$ by cyclic amplification, we preferred first to selectively concentrate the sample in the protein to be detected and to eliminate the bulk of very abundant blood proteins, such as albumin or hemoglobin. The following four different protocols have been shown effective for this purpose.

1. Preparation of Blood Cells Ghosts

Figure 11:
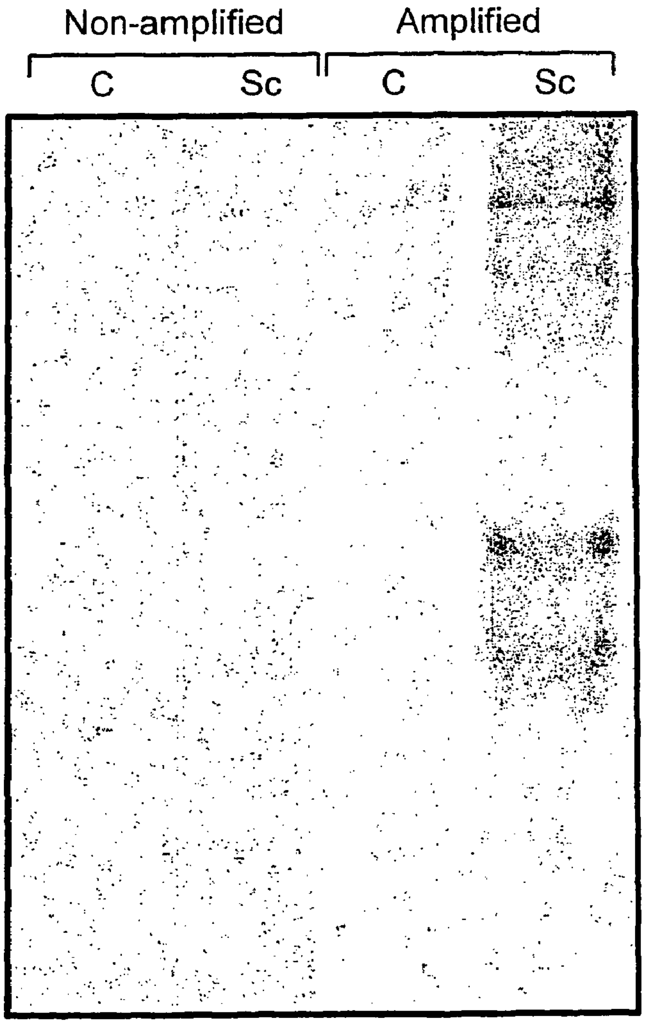
FIG. 11: Detection of PrPSc in blood after preparation of blood cells ghosts. Cell ghosts from 0.5 ml of heparinized blood coming from healthy (C) and scrapie-affected hamsters (Sc) were prepared as described in the text. Half of the samples were not subjected to amplification and the other half were mixed with normal hamster brain homogenate and subjected to 20 amplification cycles. All samples were then treated with PK and analyzed by immunoblots. One representative experiment is shown in the Figure.

Heparinized hamster blood was centrifuged at 2,500 rpm at 4° C. The plasma and cellular fraction were separated and frozen at −80° C. until needed. 0.5 ml of blood cell package was washed 3 times in 12-15 vol of fresh cold PBS, pH 7.6. The cells were resuspended in 12-15 vol of 20 mOsM sodium phosphate buffer pH 7.6 and stirred gently for 20 min on ice, then centrifuged at 30,000 rpm for 10 min at 4° C. The supernatant was discarded, the pellet was washed 3 times in 20 mOsM sodium phosphate buffer. The final pellet was resuspended in PBS containing 0.5% Triton X-100, 0.5% SDS and protease inhibitors. 15 μl of this suspension was mixed v/v with 10% healthy hamster brain homogenate and subjected to 20 cycles of incubation-sonication. 20 μl of sonicated and control samples were digested with proteinase K, separated by SDS-PAGE and analyzed by western blotting and $PrP^{Sc}$ was detected as disclosed in the "Methods" section. The results show the detection of the $PrP^{Sc}$ after the amplification procedure in the blood samples from infected animals (FIG. 11). In the blood samples from non-infected animals there is no signal after amplification. Without amplification is not possible to detect the presence of $PrP^{Sc}$ (FIG. 11).

2. Sarkosyl Extraction

Figure 12:
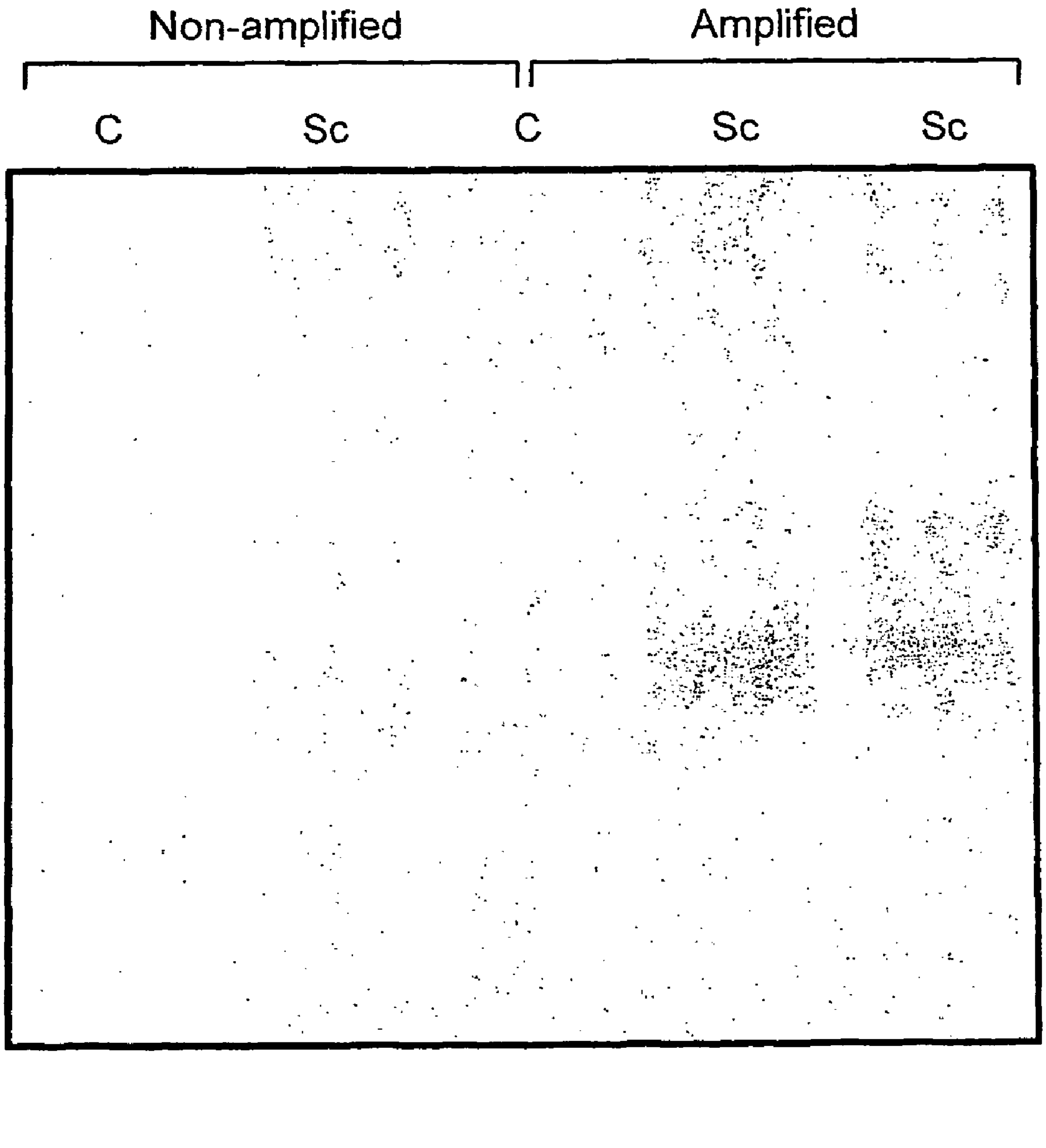
FIG. 12: Detection of PrPSc in blood after sarkosyl extraction. 0.5 ml of heparinized blood coming from healthy (C) and scrapie-affected hamsters (Sc) was subjected to sarkosyl extraction as described in the text. Half of the samples were not subjected to amplification and the other half were mixed with normal hamster brain homogenate and subjected to 20 amplification cycles. All samples were then treated with PK and analyzed by immunoblots. One representative sample of control animals and two for scrapie-affected animals is shown in the Figure.

Heparinized hamster blood was centrifuged at 2,500 rpm at 4° C. 0.5 ml of blood cell package was diluted (v/v) in 20% sarkosyl and incubated for 30 minutes. The sample was centrifuged in Beckman TL100 ultracentrifuged at 85,000 rpm for 2 hrs at 4° C. The pellet was washed and resuspended in PBS containing 0.5% Triton X-100, 0.5% SDS and protease inhibitors. 15 µl of this suspension was mixed v/v with 10% healthy hamster brain homogenate and subjected to 20 cycles of incubation-sonication. 20 µl of sonicated and control samples were digested with proteinase K, separated by SDS-PAGE and analyzed by western blotting and $PrP^{Sc}$ was detected as disclosed in the "Methods" section. The results show the detection of the $PrP^{Sc}$ after the amplification procedure in the blood samples from infected animals (FIG. 12). In the blood samples from non-infected animals there is no signal after amplification. Without amplification is not possible to detect the presence of $PrP^{Sc}$ (FIG. 12).

3. Lipid Raft Extraction

Figure 13:
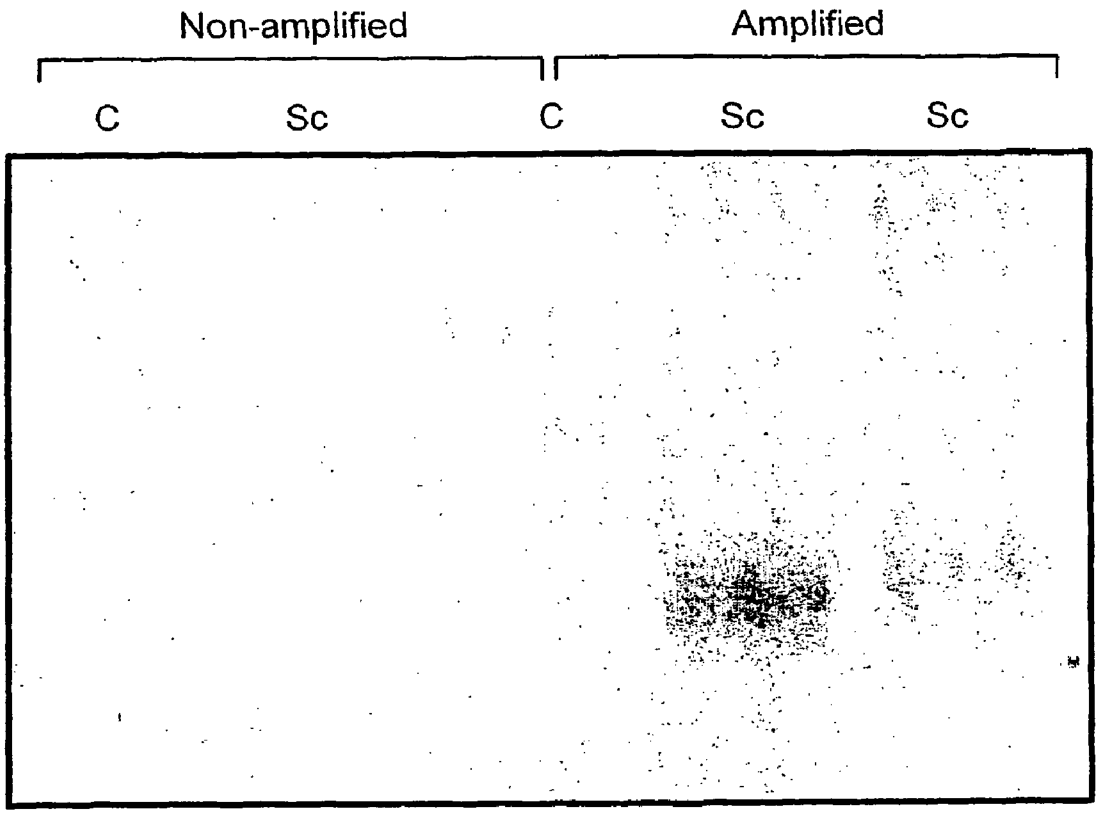
FIG. 13: Detection of PrPSc in blood after lipid rafts purification. Lipid-rafts were extracted as described in the text from 0.5 ml of heparinized blood coming from healthy (C) and scrapie-affected hamsters (Sc). Half of the samples were not subjected to amplification and the other half were mixed with normal hamster brain homogenate and subjected to 20 amplification cycles. All samples were then treated with PK and analyzed by immunoblots. One representative sample of control animals and two for scrapie-affected animals is shown in the Figure.

Heparinized hamster blood was centrifuged at 2,500 rpm at 4° C. 0.5 ml of blood cell package was diluted (v/v) in PBS with 1% Triton X-100 and incubated for 30 minutes at 4° C. The sample was diluted 1:2 in sucrose 60% and placed in the bottom of a centrifuge tube. 7 ml of sucrose 35% were placed carefully over the sample. 1.5 ml of sucrose 15% was layered in the top of the gradient. The tube was centrifuged at 150,000 rpm for 18 hrs at 4° C. The lipid rafts were recovered washed in PBS and centrifuged at 28,000 rpm during 1 hr at 4° C. The pellet was washed and resuspended in PBS containing 0.5% Triton X-100, 0.5% SDS and protease inhibitors. 15 µl of this suspension was mixed v/v with 10% healthy hamster brain homogenate and subjected to 20 cycles of incubation-sonication. 20 µl of sonicated and control samples were digested with proteinase K, separated by SDS-PAGE and analyzed by western blotting and $PrP^{Sc}$ was detected as disclosed in the "Methods" section. The results show the detection of the $PrP^{Sc}$ after the amplification procedure in the blood samples from infected animals (FIG. 13). In the blood samples from non-infected animals there is no signal after amplification. Without amplification is not possible to detect the presence of $PrP^{Sc}$ (FIG. 13).

4. Buffy Coat Preparation.

Figure 14:
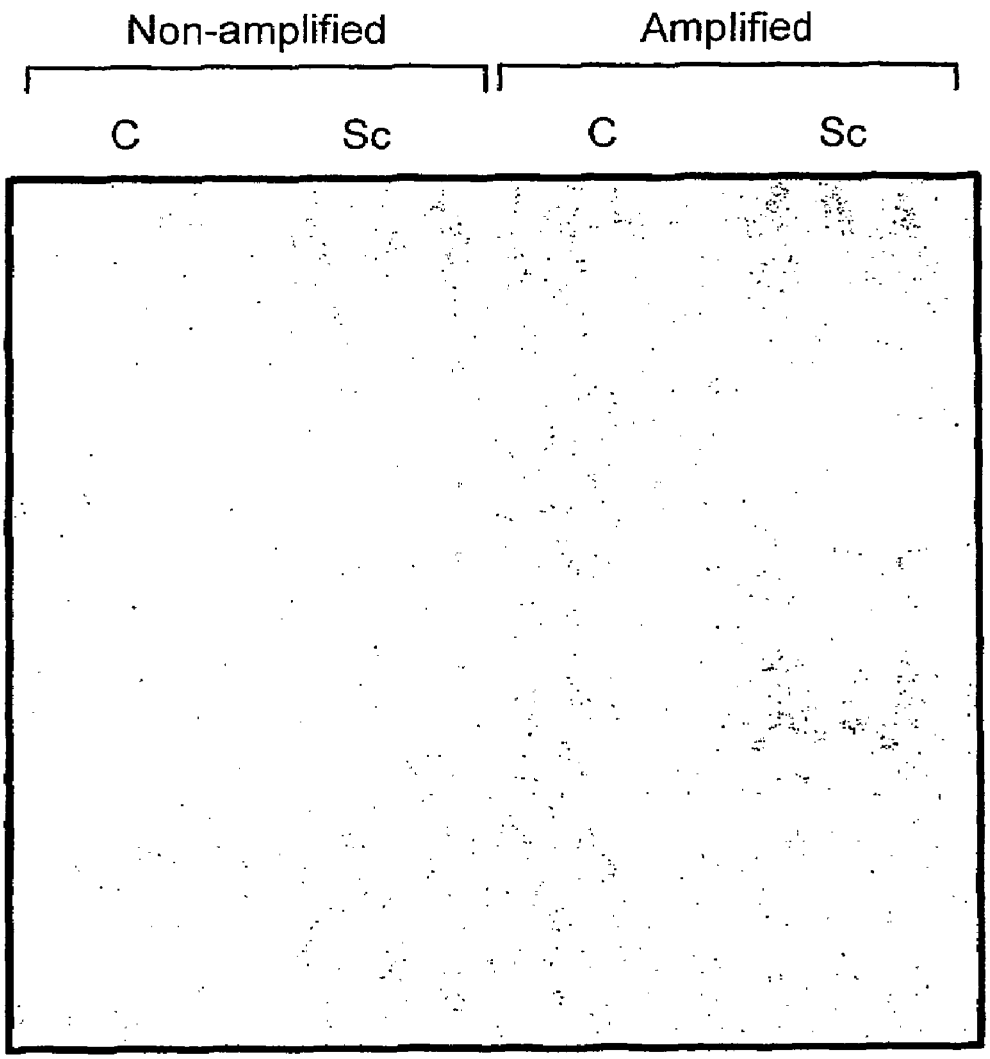
FIG. 14: Detection of PrPSc in blood after preparation of buffy coats. The buffy coat fraction of blood was separated by centrifugation from 0.5 ml of heparinized blood coming from healthy (C) and scrapie-affected hamsters (Sc). Half of the samples were not subjected to amplification and the other half were mixed with normal hamster brain homogenate and subjected to 20 amplification cycles. All samples were then treated with PK and analyzed by immunoblots. One representative experiment is shown in the Figure.

Heparinized hamster blood was centrifuged at 1,500 rpm at 4° C. for 10 min. The buffy coat was carefully recovered using standard procedures and kept at −80° C. until needed. The frozen buffy coat was resuspended in PBS containing 0.5% Triton X-100, 0.5% SDS and protease inhibitors. 15 µl of this suspension was mixed v/v with 10% healthy hamster brain homogenate and subjected to 20 cycles of incubation-sonication. 20 µl of sonicated and control samples were digested with proteinase K, separated by SDS-PAGE and analyzed by western blotting and $PrP^{Sc}$ was detected as disclosed in the "Methods" section. The results show the detection of the $PrP^{Sc}$ after the amplification procedure in the blood samples from infected animals (FIG. 14). In the blood samples from non-infected animals there is no signal after amplification. Without amplification is not possible to detect the presence of $PrP^{Sc}$ (FIG. 14).

Methods

Preparation of Brain Homogenates.

Brains from Syrian golden hamsters healthy or infected with the adapted scrapie strain 263 K were obtained after decapitation and immediately frozen in dry ice and kept at −80° C. until used. Brains were homogenized in PBS and protease inhibitors (w/v) 10%. Detergents (0.5% Triton X-100, 0.05% SDS) were added and clarified with low speed centrifugation (10,000 rpm) for 1 min.

Preparation of the Samples and Cyclic Amplification.

Serial dilutions of the scrapie brain homogenate were made directly in the healthy brain homogenate. 30 µl of these dilutions were incubated at 37° C. with agitation. Each hour a cycle of sonication (5 pulses of 1 sec each) was done using a microsonicator with the needle immersed in the sample. These cycles were repeated several times (5-20).

$PrP^{Sc}$ Detection.

The samples were digested with PK 100 µg/mL for 90 min at 37° C. The reaction was stopped with PMSF 50 mM. Samples were separated by SDS-PAGE (under denaturing conditions) and electroblotted into nitrocellulose membrane in CAPS or tris-glycine transfer buffer with 10% methanol during 45 min at 400 mA. Reversible total protein staining was performed before blocking of the membrane with 5% non-fat milk. Thereafter, the membrane was incubated for 2 hr with the monoclonal antibody 3F4 (1:50,000). Four washes of 5 min each were performed with PBS, 0.3% Tween20 before the incubation with the horseradish peroxidase labelled secondary anti-mouse antibody (1:5000) for 1 hr. After washing, the reactivity in the membrane was developed with ECL chemiluminescence Kit (Amersham) according to manufacturer's instructions.

REFERENCES

Aguzzi, A. (1997). Neuro-immune connection in the spread of prions in the body? Lancet 349, 742-744.

Baldwin, M. A., Cohen, F. E., and Prusiner, S. B. (1995). Prion protein isoforms, a convergence of biological and structural investigations. J. Biol. Chem. 270, 19197-19200.

Baslet et al., Cell_46:417-428 (1986)

Brown, P., Cervenakova, L., and Diringer, H. (2001). Blood infectivity and the prospects for a diagnostic screening test in Creutzfeldt-Jakob disease. J. Lab. Clin. Invest. 137, 5-13.

Bruce, M. E., Will, R. G., Ironside, J. W., McConnell, I., Drummond, D., and Suttie, A. (1997). Transmissions to mice indicate that new variant CJD is caused by the BSE agent. Nature 389, 498-501.

Budka, H., Aguzzi, A., Brown, P., Brucher, J. M., Bugiani, O., Gullotta, F., Haltia, M., Hauw, J. J., Ironside, J. W., Jellinger, K., Kretzschmar, H. A., Lantos, P. L., Masullo, C., Schlote, W., Tateishi, J., and Weller, R. O. (1995). Neuropathological diagnostic criteria for Creutzfeldt-Jakob disease (CJD) and other human spongiform encephalopathies (Prion diseases). Brain Pathol. 5, 459-466.

Carrell, R. W., Lomas D. A. (1997). Conformational diseases. Lancet, 350, 134-138.

Caughey, B., Raymond, G. J., Kocisko, D. A., and Lansbury, P. T., Jr. (1997). Scrapie infectivity correlates with converting activity, protease resistance, and aggregation of scrapie-associated prion protein in guanidine denaturation studies. J. Virol. 71, 4107-4110.

Cohen, F. E., Pan, K. M., Huang, Z., Baldwin, M., Fletterick, R. J., and Prusiner, S. B. (1994). Structural clues to prion replication. Science 264, 530-531.

Cohen, F. E. and Prusiner, S. B. (1998). Pathologic conformations of prion proteins. Ann. Rev. Biochem. 67, 793-819.

Cousens, S. N., Vynnycky, E., Zeidler, M., Will, R. G., and Smith, R. G. (1997). Predicting the CJD epidemic in humans. Nature 385, 197-198.

Gabriel et al., Proc. Natl. Acad. Sci. USA 89:9097-9101 (1992)

Galvez, S. and Cartier, L. (1983). Computed tomography findings in 15 cases of Creutzfeldt-Jakob disease with histological verification. J. Neurol. Neurosurg. Psychiatry 47, 1244.

Goldmann et al., *Proc. Natl. Acad. Sci. USA* 87:2476-2480 (1990).

Goldmann et al., *J. Gen. Virol.* 72:201-204 (1991).

Harmey, J. H., Doyle, D., Brown, V., and Rogers, M. S. (1995). The cellular isoform of the prion protein, PrPc, is associated with caveolae in mouse neuroblastoma (N2a) cells. Biochem. Biophys. Res. Comm. 210, 753-759.

Harris et al., *Proc. Natl. Acad. Sci. USA* 88:7664-7668 (1991).

Hill, A. F., Zeidler, M., Ironside, J. W., and Collinge, J. (1997). Diagnosis of new variant Creutzfeldt-Jakob disease by tonsil biopsy. Lancet 349, 99-100.

Hsich, G., Kenney, K., Gibbs, C. J., Jr., Lee, K. H., and Harrington, M. G. (1996). The 14-3-3 brain protein in cerebrospinal fluid as a marker for transmissible spongiform encephalopathies. N. Eng. J. Med. 335, 924.

Jarrett, J. T. and Lansbury, P. T., Jr. (1993). Seeding "one-dimensional crystallization" of amyloid: a pathogenic mechanism in Alzheimer's disease and scrapie? Cell 73, 1055-1058.

Jimi, T., Wakayama, Y., Shibuya, S., and et al (1992). High levels of nervous system specific protein in the cerebrospinal fluid in patients with early stage Creutzfeldt-Jakob disease. Clin. Chim. Acta 211, 37.

Kawashima, T., Furukawa, H., Doh-ura, K., and Iwaki, T. (1997). Diagnosis of new variant Creutzfeldt-Jakob disease by tonsil biopsy. Lancet 350, 68-69.

Kascsak R J, Rubenstein R, Merz P A, Tonna-DeMasi M, Fersko R, Carp R I, Wisnieswski H M, Diringer H, (1987). Mouse polyclonal and monoclonal antibody to scarpie-associated fibril proteins. J. Virol., 61, 3688-3693.

Kocisko, D. A., Come, J. H., Priola, S. A., Chesebro, B., Raymond, G. J., Lansbury, P. T., and Caughey, B. (1994). Cell-free formation of protease-resistant prion protein. Nature 370, 471-474.

Kocisko, D. A., Priola, S. A., Raymond, G. J., Chesebro, B., Lansbury, P. T., Jr., and Caughey, B. (1995). Species specificity in the cell-free conversion of prion protein to protease-resistant forms: a model for the scrapie species barrier. Proc. Natl. Acad. Sci. USA 92, 3923-3927.

Kretzschmar et al., *DNA* 5:315-324 (1986).

Kretzschmar et al., *J. Gen. Virol.* 73:2757-2761 (1992).

Locht et al., *Proc. Natl. Acad. Sci. USA* 83:6372-6376 (1986).

Onofrji, M., Fulgente, T., Gambi, D., and Macchi, G. (1993). Early MRI findings in Creutzfeld-Jakob disease. J. Neurol. 240, 423.

Pan, K. M., Baldwin, M., Njuyen, J., Gassett, M., Serban, A., Groth, D., Mehlhorn, I., and Prusiner, S. B. (1993). Conversion of alpha-helices into □□-sheets features in the formation of scrapie prion poteins. Proc. Natl. Acad Sci. (USA) 90, 10962-10966.

Prusiner, S. B. (1991). Molecular biology of prion diseases. Science 252, 1515-1522.

Roos, R., Gajdusek, D. C., and Gibbs, C. J., Jr. 1973). The clinical characteristics of trnsmissible Creutzfeldt-Jakob disease. Brain 96, 1-20.

Saborio, G. P., Soto, C., Kascsak, R. J., Levy, E., Kascsak, R., Harris, D. A., and Frangione, B. (1999). Cell-lysate conversion of prion protein into its protease-resistant isoform suggests the participation of a cellular chaperone. Biochem. Biophys. Res. Commun. 258, 470-475.

Safar J, Wille H, Itri V, Groth D, Serban H, Torchia M, Cohen F E, Prusiner S B, (1998). Eight prion strains have PrP(Sc) molecules with different conformations. Nat. Med. 4, 1157-1165.

Sargiacomo M, Sudol M, Tang Z, Lisanti M P. (1993), Signal transducing molecules and glycosyl-phosphatidylinositol-linked proteins form a caveolin-rich insoluble complex in MDCK cells., J Cell Biol. Aug; 122(4):789-807

Stahl, N., Baldwin, M. A., Teplow, D. B., Hood, L., Gibson, B. W., Burlingame, A. L., and Prusiner, S. B. (1993). Structural studies of the scrapie prion protein using mass spectrometry and amino acid sequencing. Biochem. 32, 1991-2002.

Steinhoff, B. J., Räcker, S., Herrendorf, G., and et al (1996). Accuracy and reliability of periodic sharp wave complexes in Creutzfeldt-Jakob disease. Arch. Neurol. 53, 162.

Telling, G. C., Scott, M., Mastrianni, J., Gabizon, R., Torchia, M., Cohen, F. E., DeArmond, S. J., and Prusiner, S. B. (1995). Prion propagation in mice expressing human and chimeric PrP transgenes implicates the interaction of cellular PrP with another protein. Cell 83, 79-90.

Martin Vey et al. (1996), Pro. Natl. Acad. Sci. USA, 93, 14945-9

Weber, T., Otto, M., Bodemer, M., and Zerr, I. (1997). Diagnosis of Creutzfeld-Jakob disease and related human spongiform encephalopathies. Biomed. Pharmacother. 51, 381-387.

Westaway et al., *Genes Dev.* 8:959-969 (1994).

WHO/EMC/ZDI/98.9, Global Surveillance, Diagnosis and Therapy of Human Transmissible Spongiform Encephalopathies: Report of a WHO Consultation, Geneva, Switzerland 9-11 Feb. 1998, WHO.

The invention claimed is:

1. A method for the detection of a conformational disease which is characterized by a conformational transition of Prion Protein between the $PrP^{C}$ non-pathogenic conformer and the $PrP^{SC}$ pathogenic conformer, by assaying a marker of said disease within a sample, which method comprises:

(i) contacting said sample with an amount of the $PrP^{C}$ non-pathogenic conformer;

(ia) incubating said sample with said $PrP^{C}$ non-pathogenic conformer;

(ii) disaggregating any aggregates eventually formed during step (i); and (iii) determining the presence and/or amount of said $PrP^{SC}$ pathogenic conformer within the sample, the pathogenic conformer being a marker for the presence of said disease, wherein steps (ia) and (ii) form a cycle which is repeated at least twice before carrying out step (iii).

2. The method of claim 1, wherein the cycle is repeated from 5 to 40 times before carrying out step (iii).

3. The method of claim 1, wherein step (i) is carried out under physiological conditions.

4. The method of claim 1, wherein the amount of the $PrP^{C}$ non-pathogenic conformer in step (i) is an excess amount.

5. The method of claim 1, wherein the conformational disease is a transmissible conformational disease.

6. The method of any one of the preceding claims, wherein the sample to be analysed is subjected to a pre-treatment for selectively concentrating the $PrP^{SC}$ pathogenic conformer in the sample.

7. The method of claim 6, wherein the pre-treatment is the extraction from the sample of a fraction which is insoluble in mild detergents.

8. An assay for a marker of a conformational disease which is characterized by a conformational transition of Prion Protein between the $PrP^{C}$ non-pathogenic conformer and the $PrP^{SC}$ pathogenic conformer, within a sample, which assay comprises the following steps:

(i) contacting said sample with an amount of the $PrP^{C}$ non-pathogenic conformer;

(ia) incubating said sample with said $PrP^{C}$ non-pathogenic conformer;

(ii) disaggregating any aggregates eventually formed during step (i); and (iii) determining the presence and/or amount of said $PrP^{SC}$ pathogenic conformer within the sample, the $PrP^{SC}$ pathogenic conformer being a marker for the presence of said disease, wherein steps (ia) and (ii) form a cycle which is repeated at least twice before carrying out step (iii).

9. A kit for use in the assay of claim 8 which comprises a known amount of the non-pathogenic conformer, a multi-well microtitre plate and a multi-well sonicator.

10. A method for identifying a compound which modulates the conformational transition of Prion Protein between the $PrP^{C}$ non-pathogenic conformer and the $PrP^{SC}$ pathogenic conformer, comprising:

(i) contacting an amount of the $PrP^{C}$ non-pathogenic conformer with an amount of the $PrP^{SC}$ pathogenic conformer (a) in the presence of said compound and (b) in the absence of said compound;

(ii) disaggregating any aggregates eventually formed during step (i); and (iii) determining the amount of the $PrP^{SC}$ pathogenic conformer (a) in the presence of said compound and (b) in the absence of said compound.

11. A method for detecting the presence of a $PrP^{SC}$ pathogenic form of Prion Protein within a sample, comprising:

(i) contacting the sample with an amount of the $PrP^{C}$ non-pathogenic prion protein;

(ia) incubating the sample with the $PrP^{C}$ non-pathogenic prion protein;

(ii) disaggregating any aggregates formed during step (ia); repeating steps (ia)-(ii) two or more times; and then (iii) determining the presence and/or amount of $PrP^{SC}$ pathogenic prion protein within the sample.

12. Apparatus for use in the method of any one of claims 1 and 2-7 or for use in the assay of claim 8, comprising a microtitre plate, multi-well sonicator and an amount of the $PrP^{C}$ non-pathogenic conformer.

* * * * *